(12) United States Patent
Machida et al.

(10) Patent No.: US 9,964,635 B2
(45) Date of Patent: May 8, 2018

(54) PRODUCTION METHOD FOR ULTRASONIC PROBE, ULTRASONIC PROBE, AND ULTRASONIC DIAGNOSIS DEVICE

(71) Applicant: HITACHI, LTD., Tokyo (JP)

(72) Inventors: Shuntaro Machida, Tokyo (JP); Akifumi Sako, Tokyo (JP); Taiichi Takezaki, Tokyo (JP); Yasuhiro Yoshimura, Tokyo (JP); Tatsuya Nagata, Tokyo (JP); Naoaki Yamashita, Tokyo (JP); Hiroki Tanaka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 516 days.

(21) Appl. No.: 14/652,039

(22) PCT Filed: Nov. 29, 2013

(86) PCT No.: PCT/JP2013/082270
§ 371 (c)(1),
(2) Date: Jun. 12, 2015

(87) PCT Pub. No.: WO2014/091951
PCT Pub. Date: Jun. 19, 2014

(65) Prior Publication Data
US 2015/0323657 A1    Nov. 12, 2015

(30) Foreign Application Priority Data

Dec. 14, 2012 (JP) .................................. 2012-273688

(51) Int. Cl.
*G01S 7/52* (2006.01)
*A61B 8/00* (2006.01)
(Continued)

(52) U.S. Cl.
CPC ........ *G01S 7/52079* (2013.01); *A61B 8/4444* (2013.01); *A61B 8/4494* (2013.01);
(Continued)

(58) Field of Classification Search
CPC ....... A61B 8/4444; A61B 8/4494; A61B 8/54; B06B 1/0292; G01S 7/52079; G01S 15/8915; B81C 1/00301
See application file for complete search history.

(56) References Cited

U.S. PATENT DOCUMENTS 6,320,239 B1    11/2001  Eccardt et al.
7,736,985 B2 *   6/2010  Enomoto ............ G01S 7/52079
                                                         257/416
(Continued)

FOREIGN PATENT DOCUMENTS

JP    2001-502871 A    2/2001
JP    2008-008729 A    1/2008
(Continued)

OTHER PUBLICATIONS

International Search Report from International Patent Application No. PCT/JP2013/082270, dated Jan. 7, 2014.

*Primary Examiner* — Daniel Pihulic
(74) *Attorney, Agent, or Firm* — Miles & Stockbridge P.C.

(57) ABSTRACT

Both controlling damage when assembling an ultrasonic probe using a chip formed with a capacitive ultrasonic transducer and securing operational reliability are achieved. In a semiconductor substrate on which the capacitive ultrasonic transducer (CMUT) is formed on a first primary surface, a protective film is formed on the surface of the ultrasonic transducer which is formed on the first primary surface of the semiconductor substrate which is then thinned by polishing a second primary surface opposite to the first primary surface of the semiconductor substrate, an ultra- (Continued)

sonic transducer chip is cutout of the semiconductor substrate, a sound absorbing material is provided on the surface opposite to the surface formed with the ultrasonic transducer, and the protective film formed on the surface of the ultrasonic transducer is removed.

11 Claims, 39 Drawing Sheets

(51) Int. Cl.
*B81C 1/00* (2006.01)
*B06B 1/02* (2006.01)
*G01S 15/89* (2006.01)

(52) U.S. Cl.
CPC ........ *B06B 1/0292* (2013.01); *B81C 1/00301* (2013.01); *G01S 15/8915* (2013.01); *A61B 8/54* (2013.01)

(56) References Cited

U.S. PATENT DOCUMENTS

| | | | |
|---|---|---|---|
| 2008/0001239 A1* | 1/2008 | Enomoto | G01S 7/52079 438/51 |
| 2009/0301200 A1 | 12/2009 | Tanaka et al. | |
| 2009/0313809 A1* | 12/2009 | Kato | H04R 31/00 29/594 |
| 2011/0071396 A1* | 3/2011 | Sano | A61L 38/4455 29/594 |
| 2014/0276087 A1* | 9/2014 | Corl | A61B 8/4494 600/467 |
| 2015/0323657 A1* | 11/2015 | Machida | A61L 38/4444 438/51 |

FOREIGN PATENT DOCUMENTS

| | | | | |
|---|---|---|---|---|
| JP | 2012-023735 A | | 2/2012 | |
| JP | 2014120874 A | * | 6/2014 | ........... A61B 8/4444 |
| WO | WO-2014091951 A1 | * | 6/2014 | ........... A61B 8/4444 |

* cited by examiner

[Fig. 1]
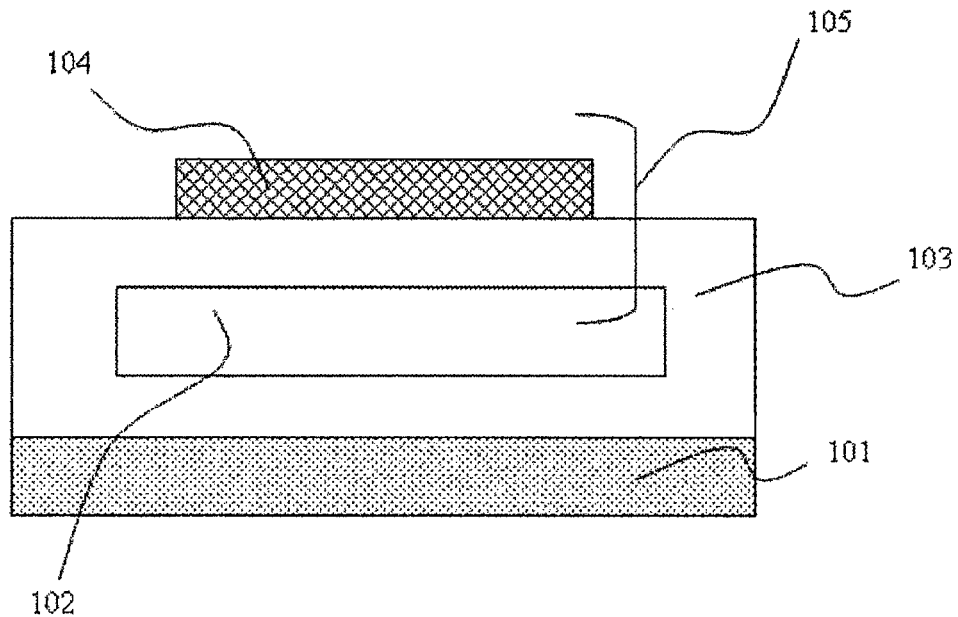
[Fig. 2]
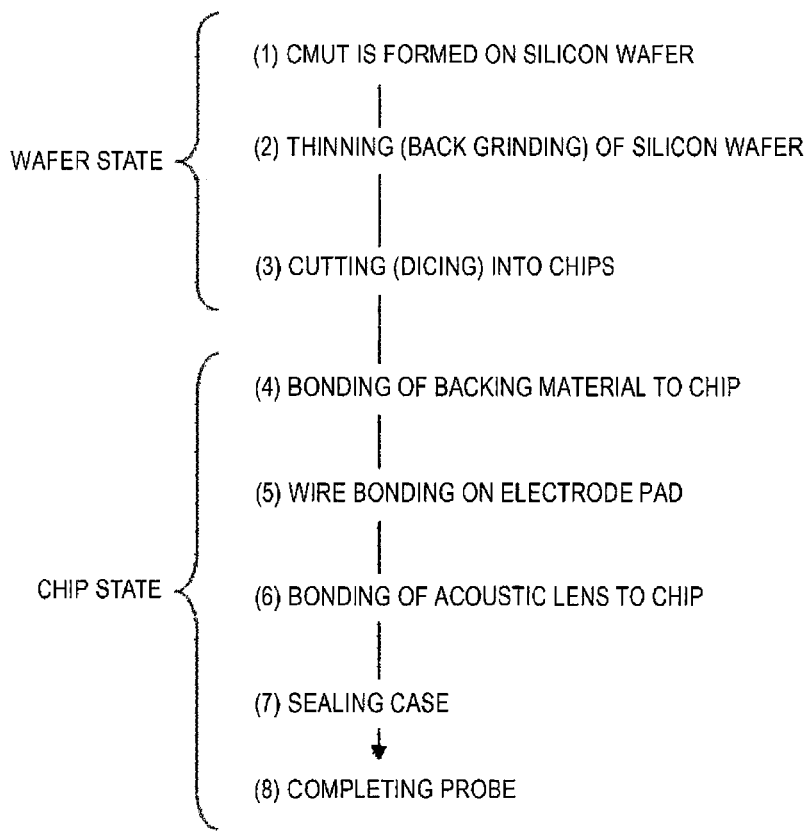

[Fig. 3]
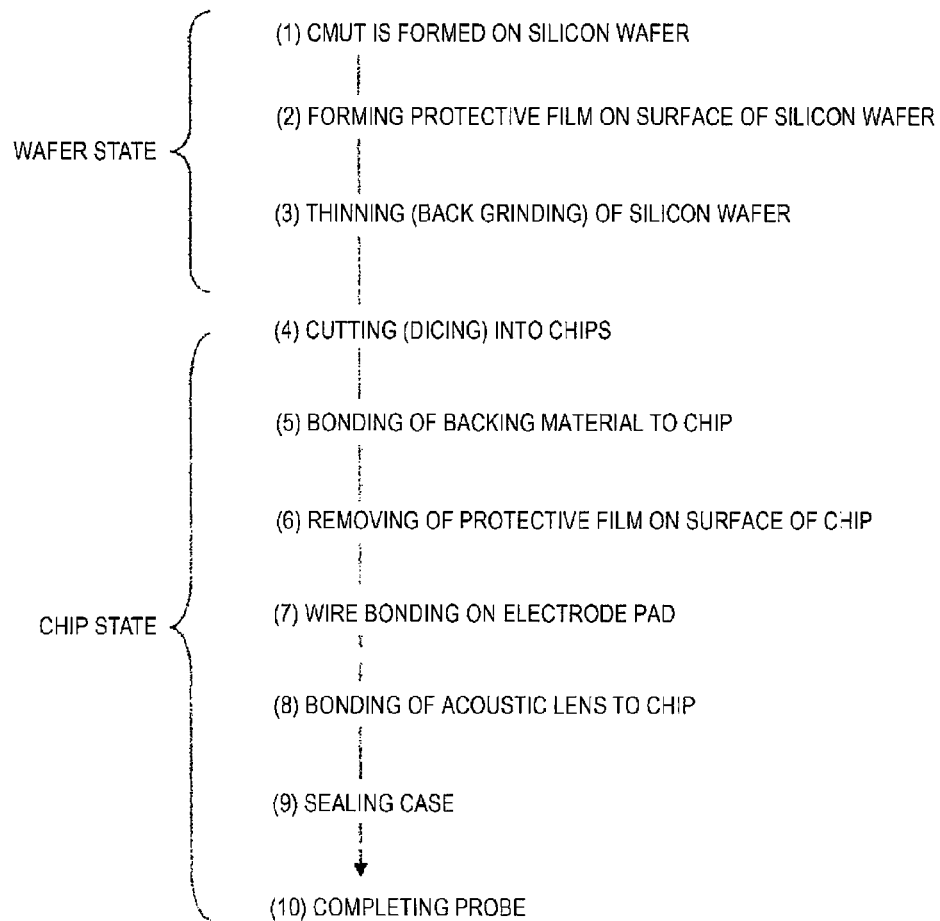
WAFER STATE
- (1) CMUT IS FORMED ON SILICON WAFER
- (2) FORMING PROTECTIVE FILM ON SURFACE OF SILICON WAFER
- (3) THINNING (BACK GRINDING) OF SILICON WAFER
CHIP STATE
- (4) CUTTING (DICING) INTO CHIPS
- (5) BONDING OF BACKING MATERIAL TO CHIP
- (6) REMOVING OF PROTECTIVE FILM ON SURFACE OF CHIP
- (7) WIRE BONDING ON ELECTRODE PAD
- (8) BONDING OF ACOUSTIC LENS TO CHIP
- (9) SEALING CASE
- (10) COMPLETING PROBE
[Fig. 4A]
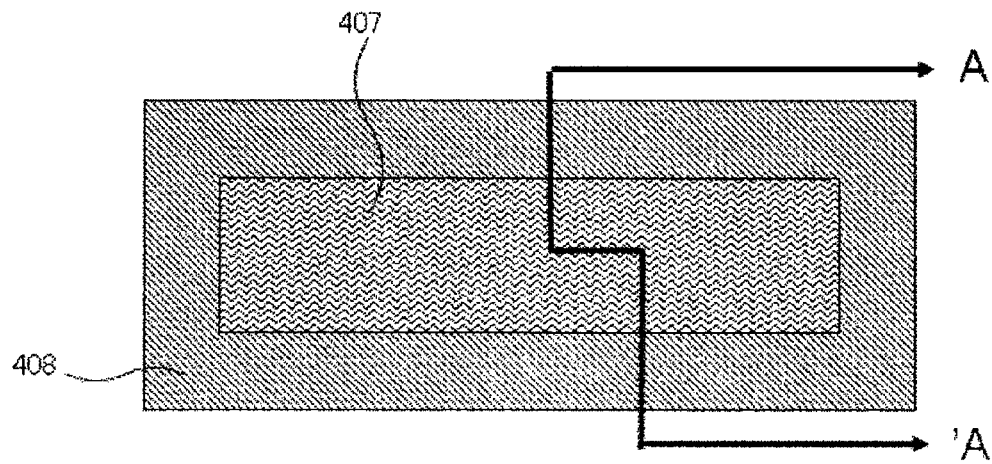

[Fig. 4B]
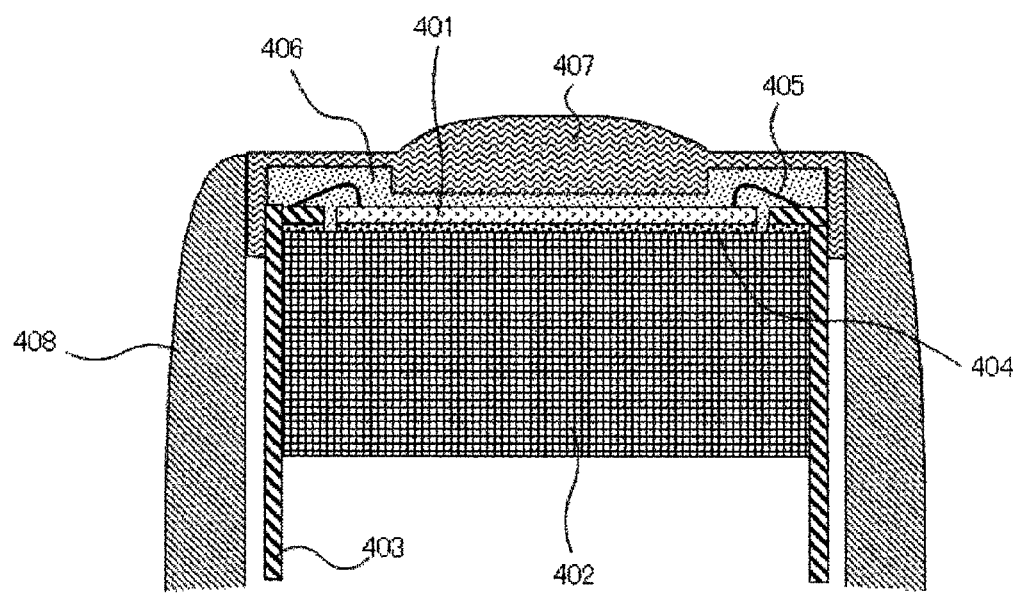

[Fig. 5]
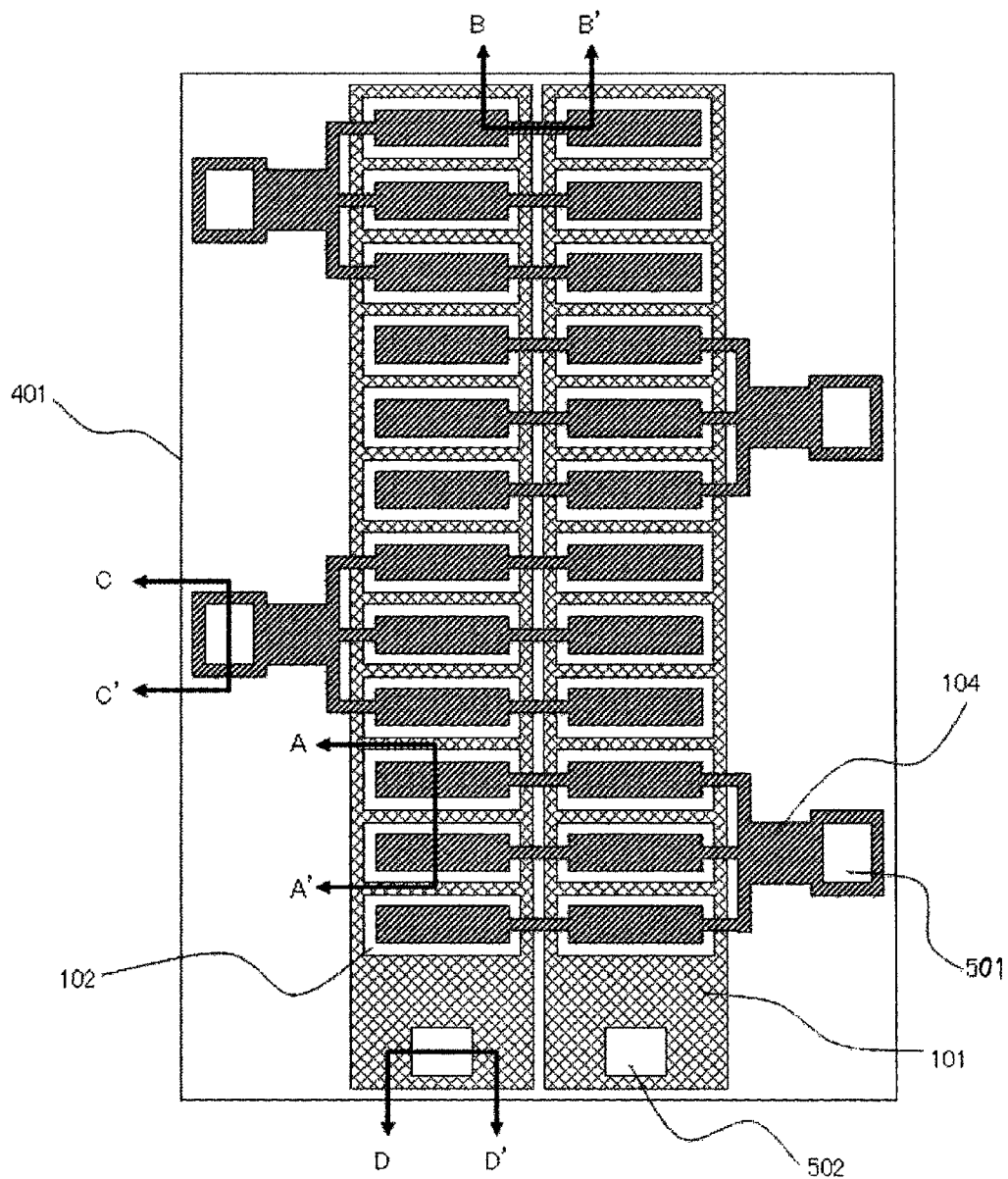

[Fig. 6A]
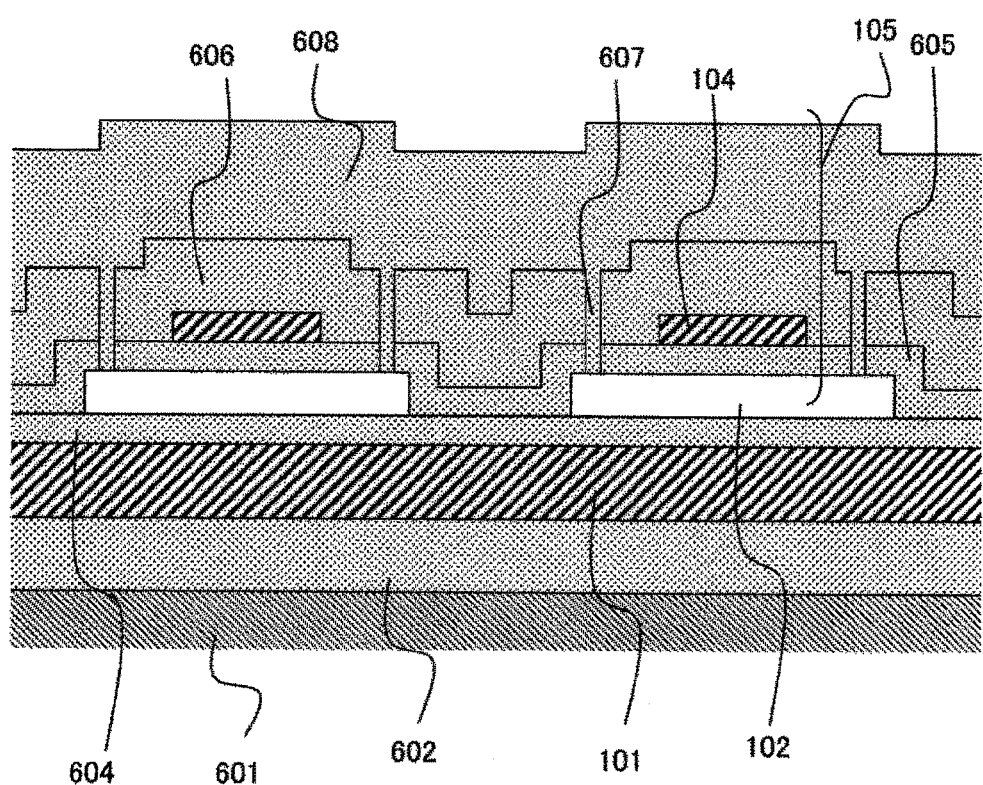

[Fig. 6B]
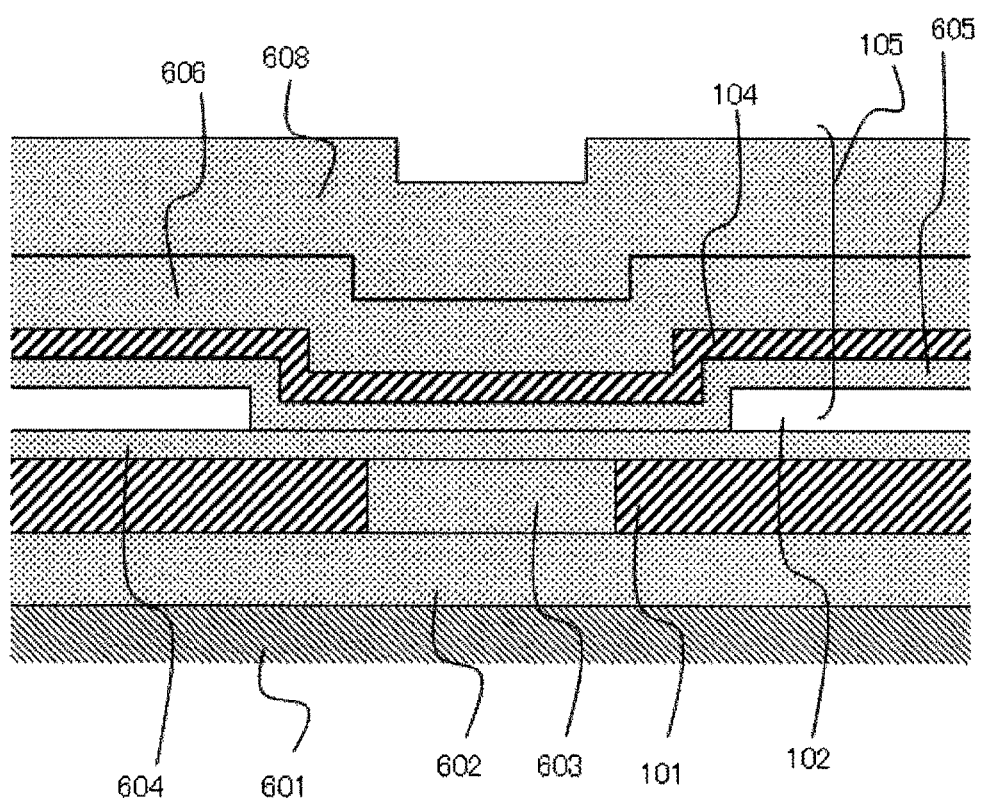

[Fig. 6C]
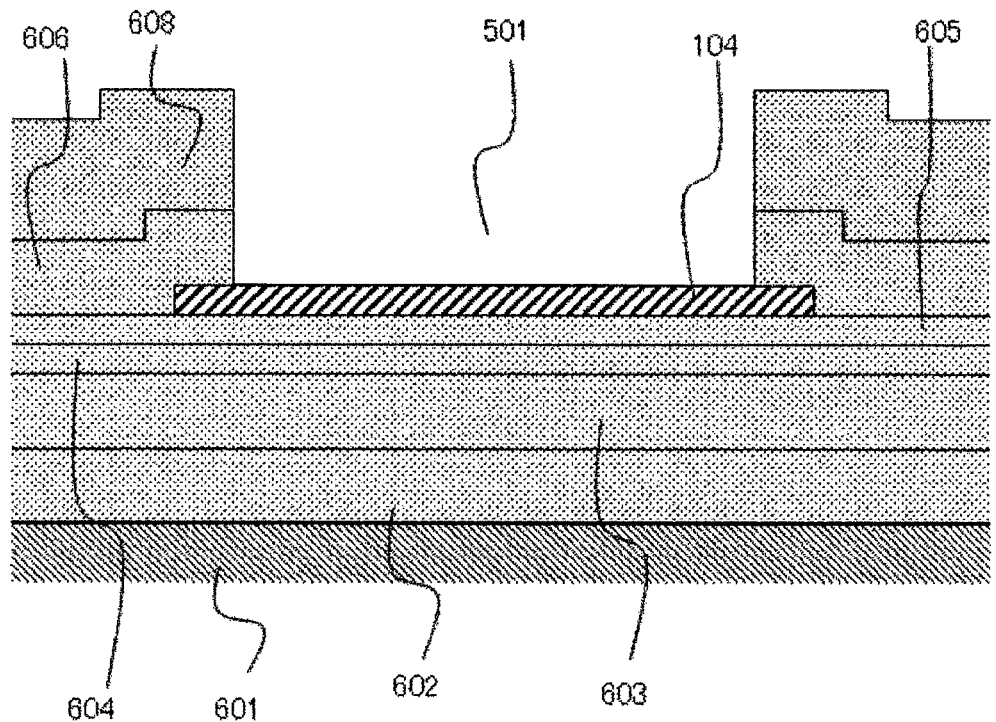
[Fig. 6D]
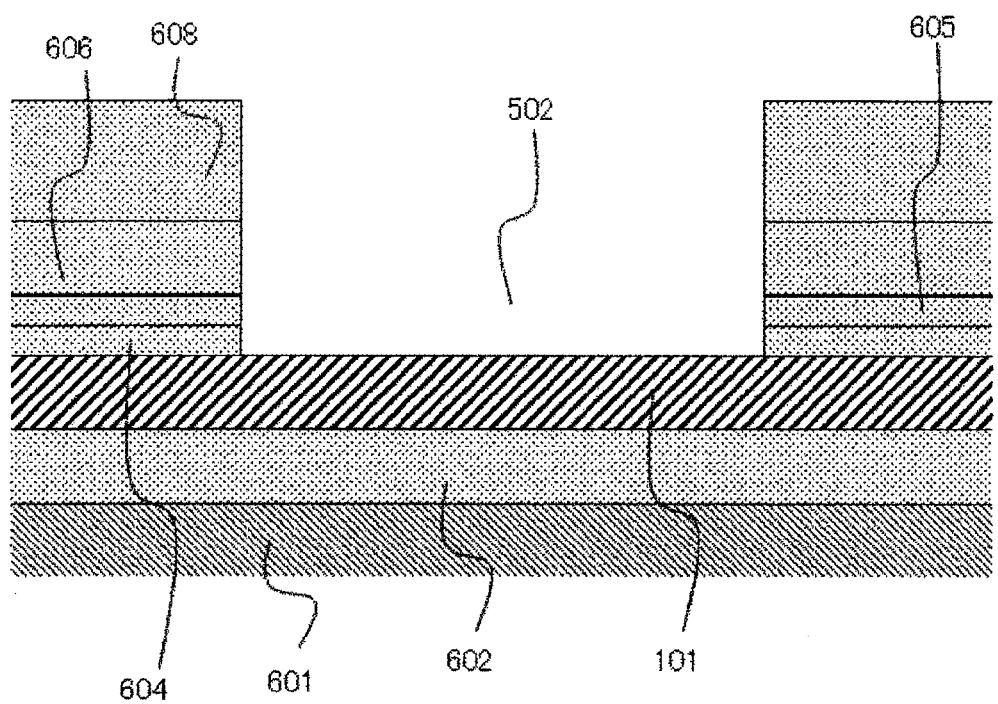

[Fig. 7]
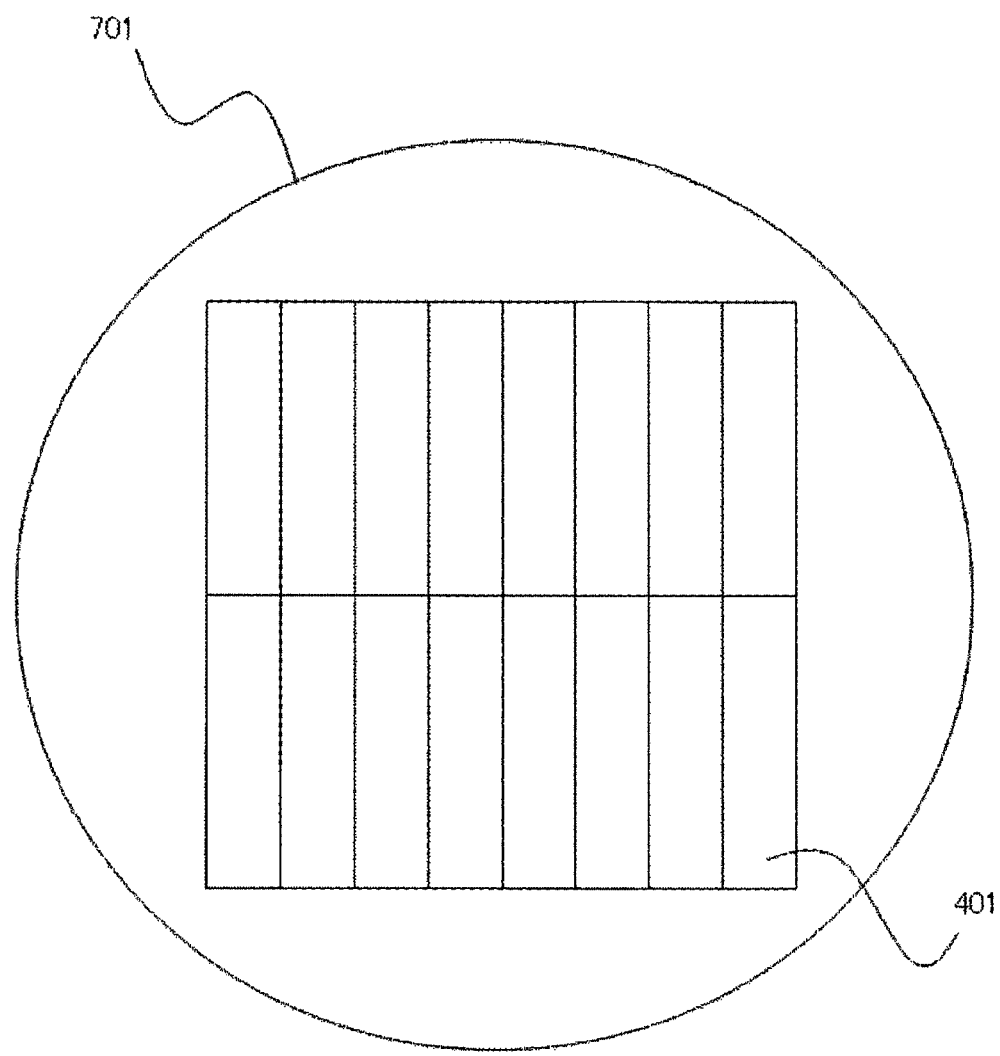

[Fig. 8]
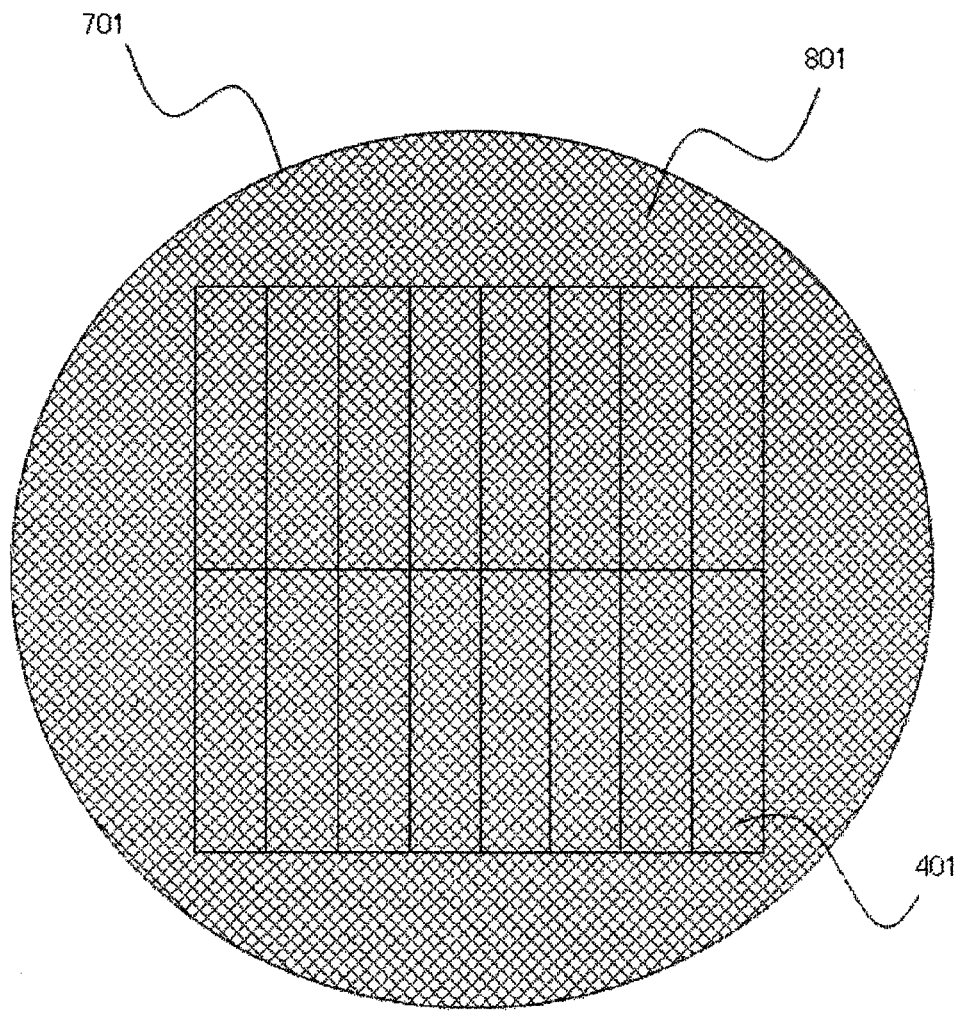

[Fig. 9A]
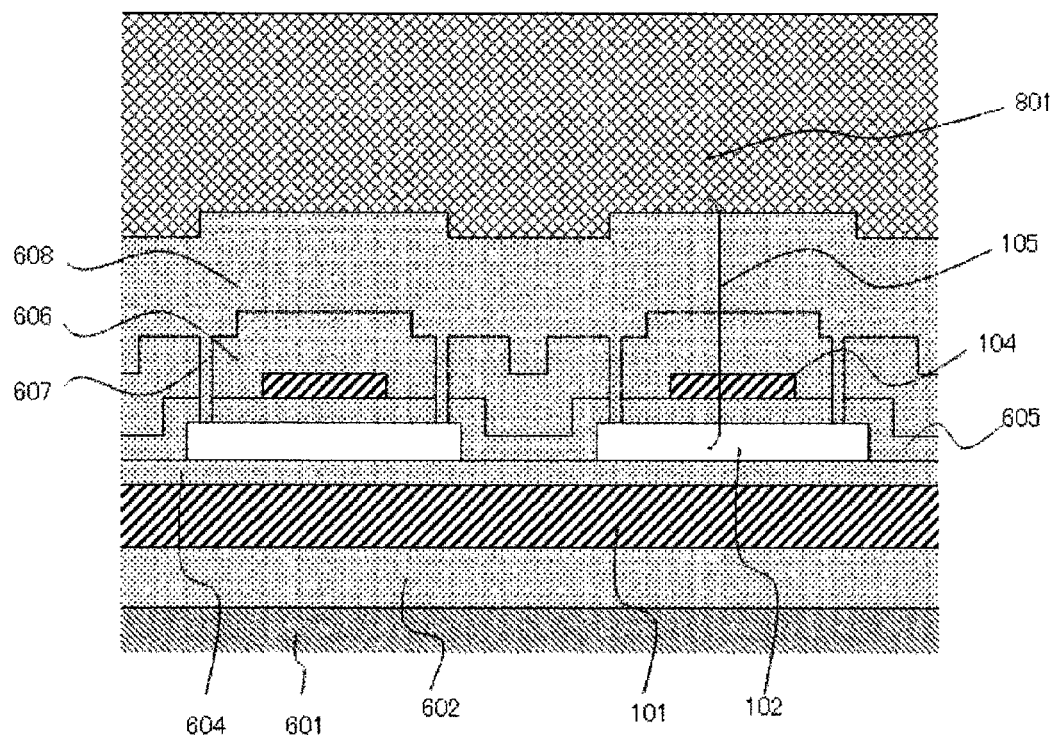

[Fig. 9B]
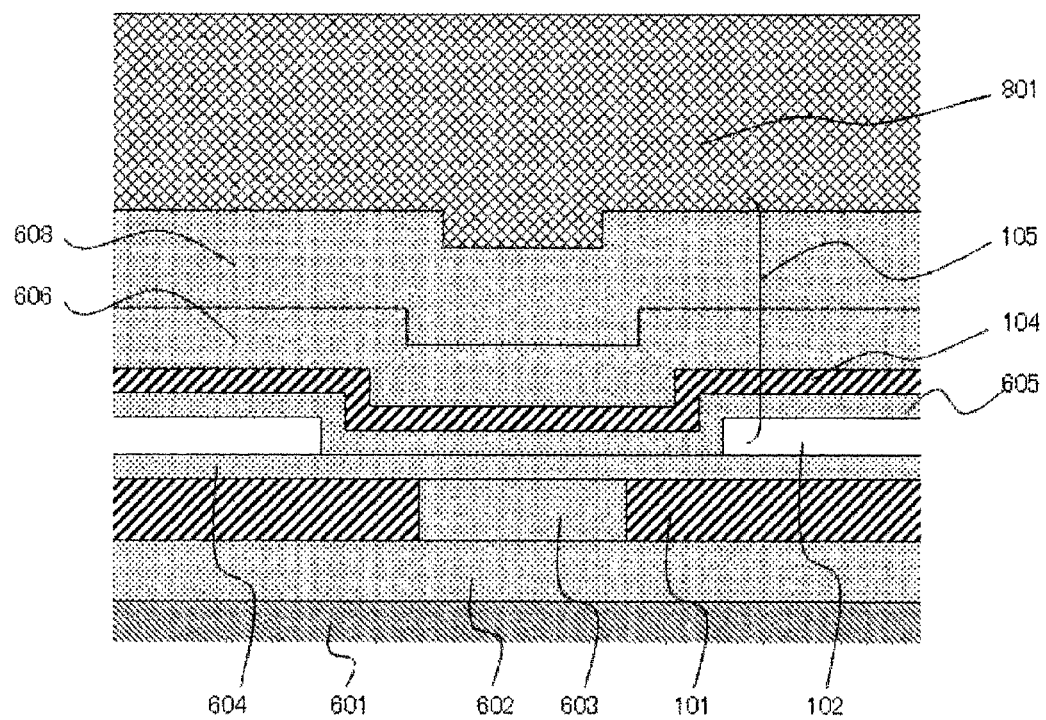

[Fig. 9C]
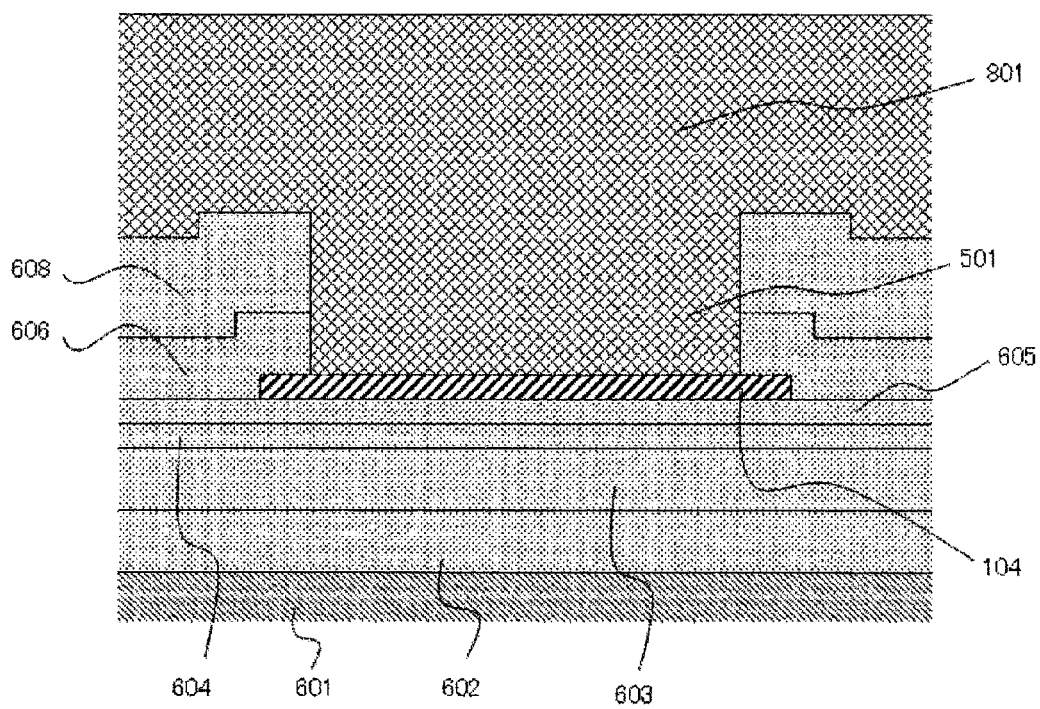

[Fig. 9D]
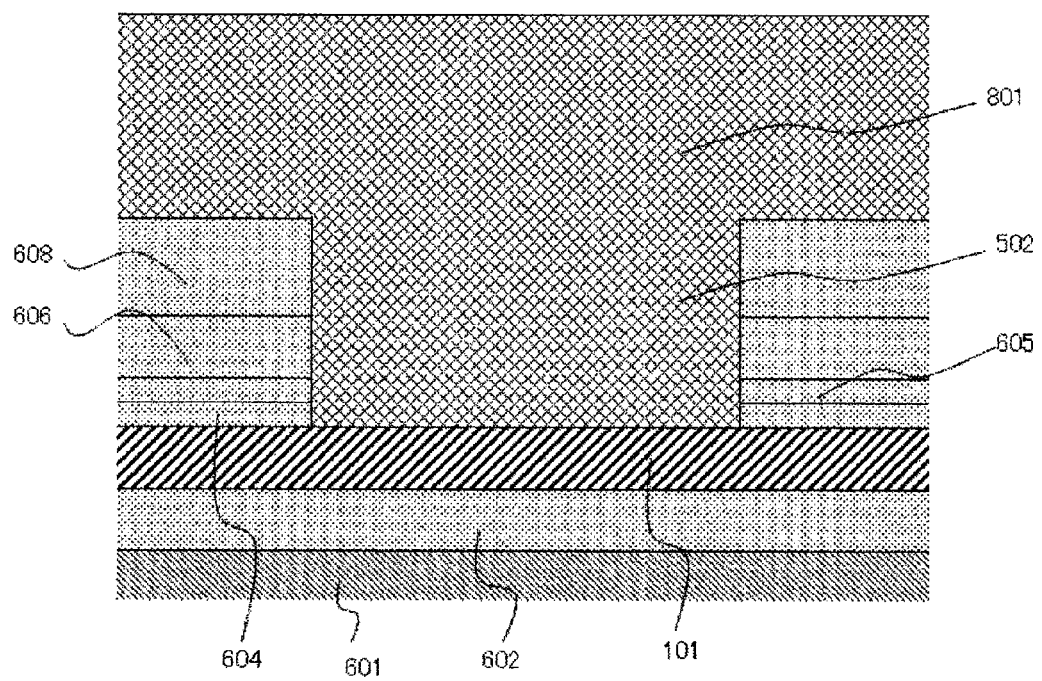

[Fig. 10A]
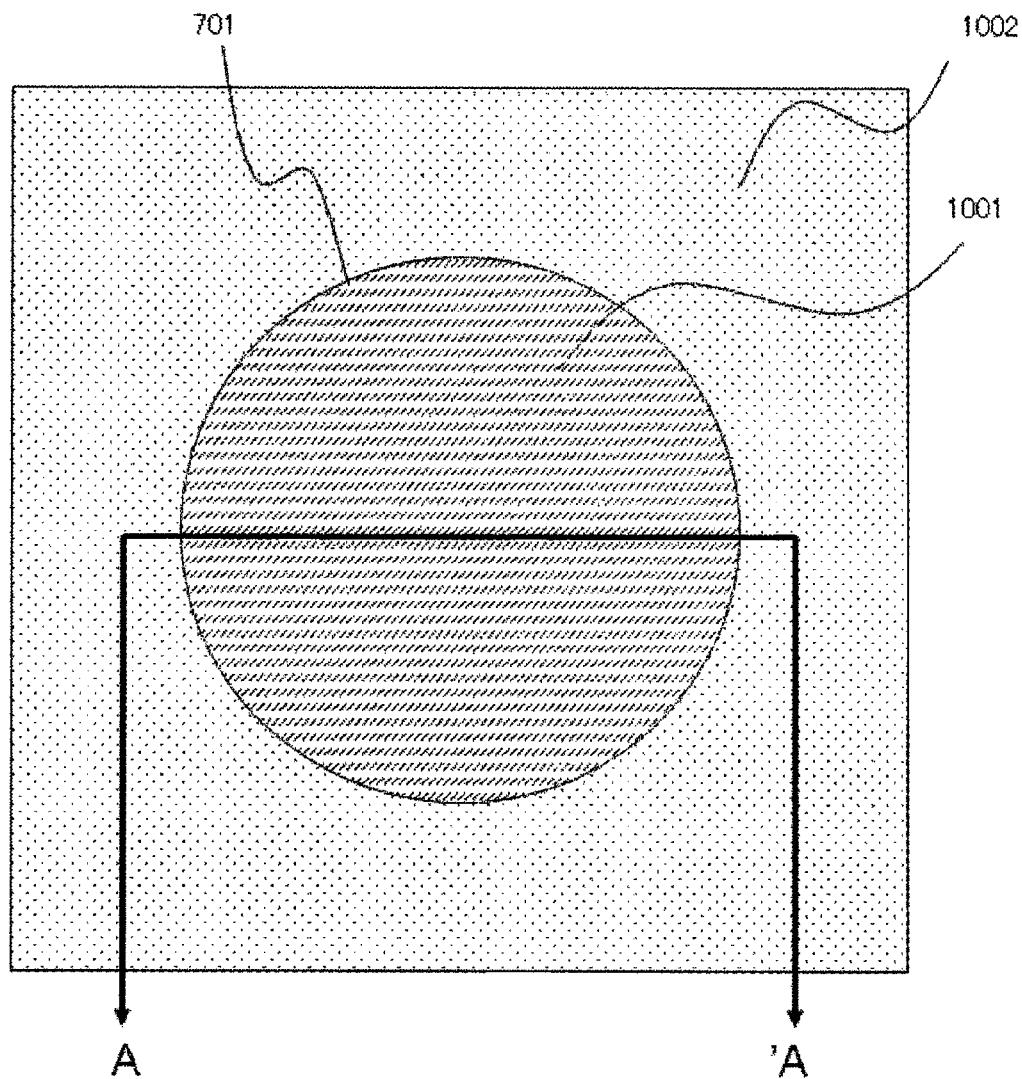
[Fig. 10B]
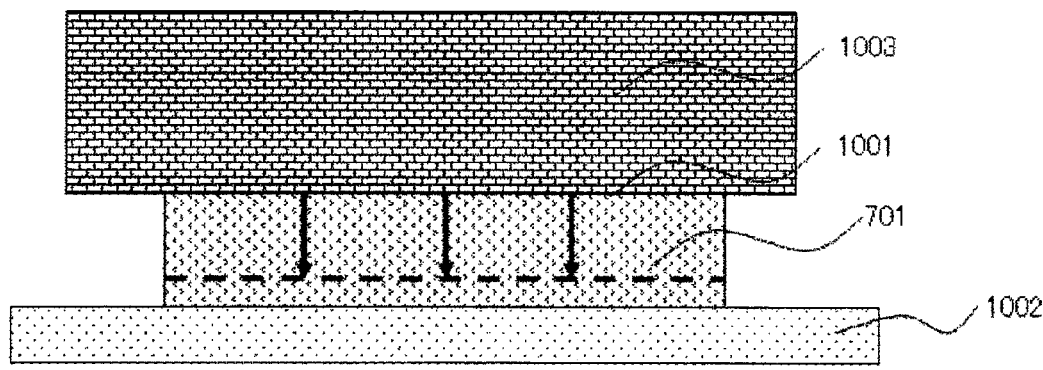

[Fig. 11A]
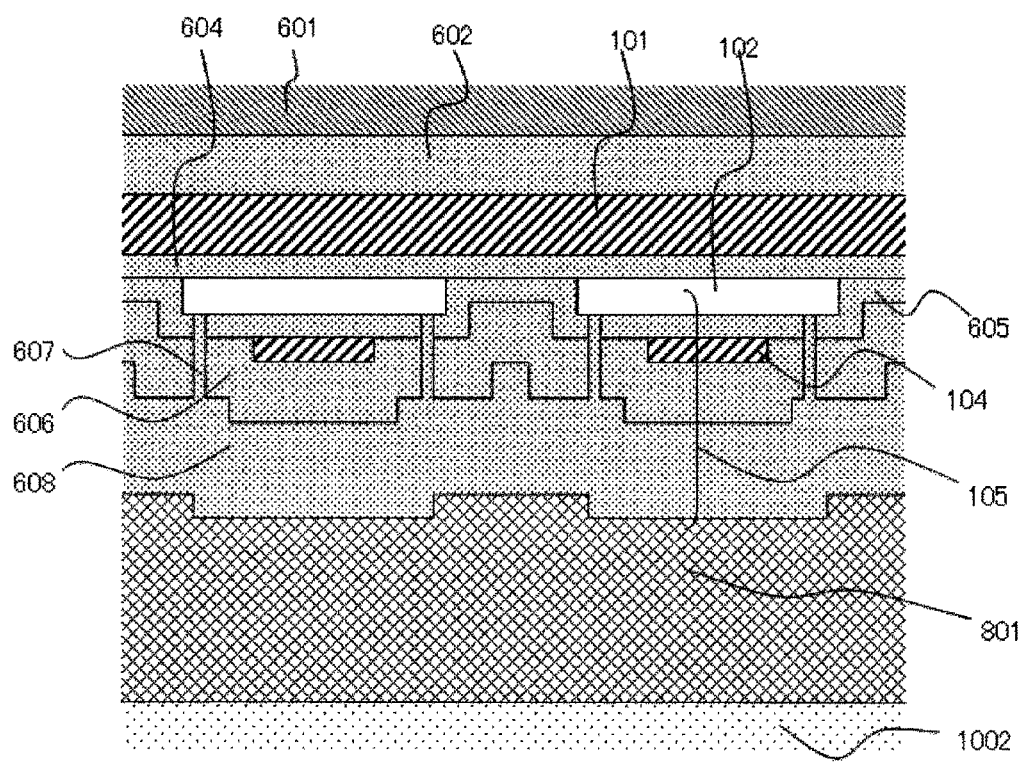

[Fig. 11B]
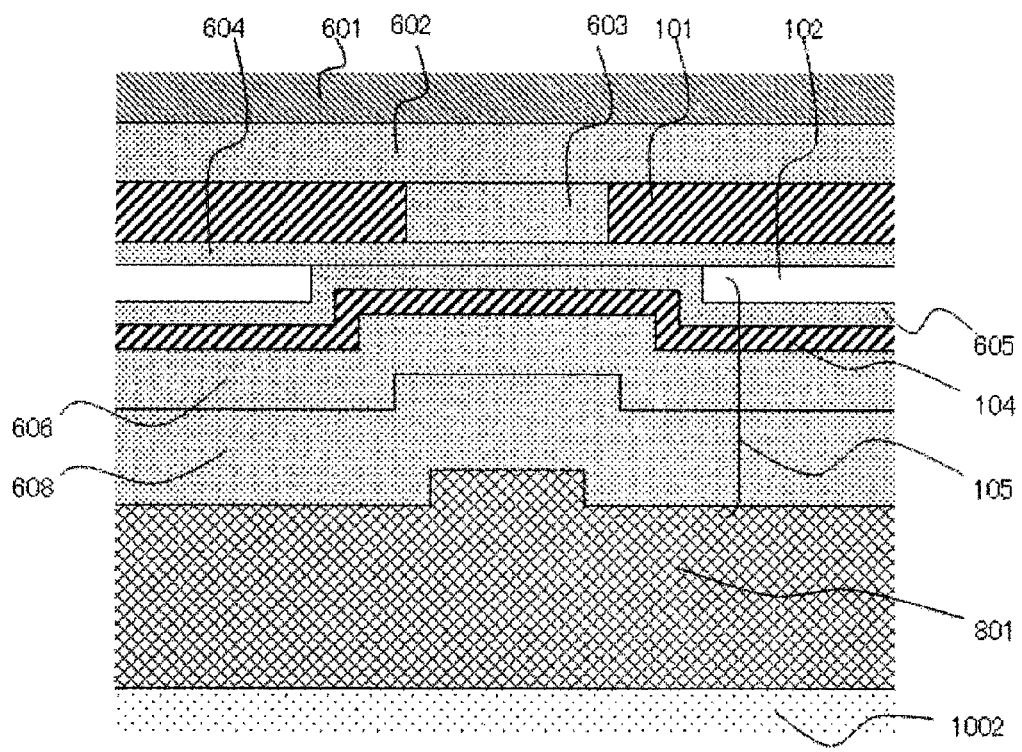

[Fig. 11C]
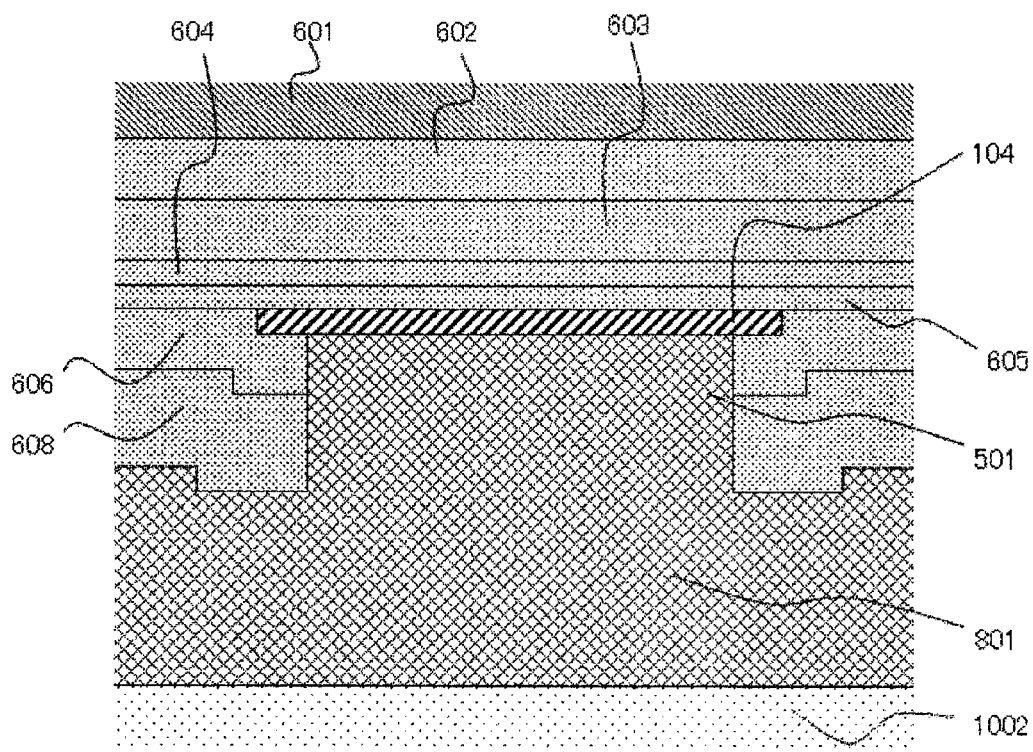

[Fig. 11D]
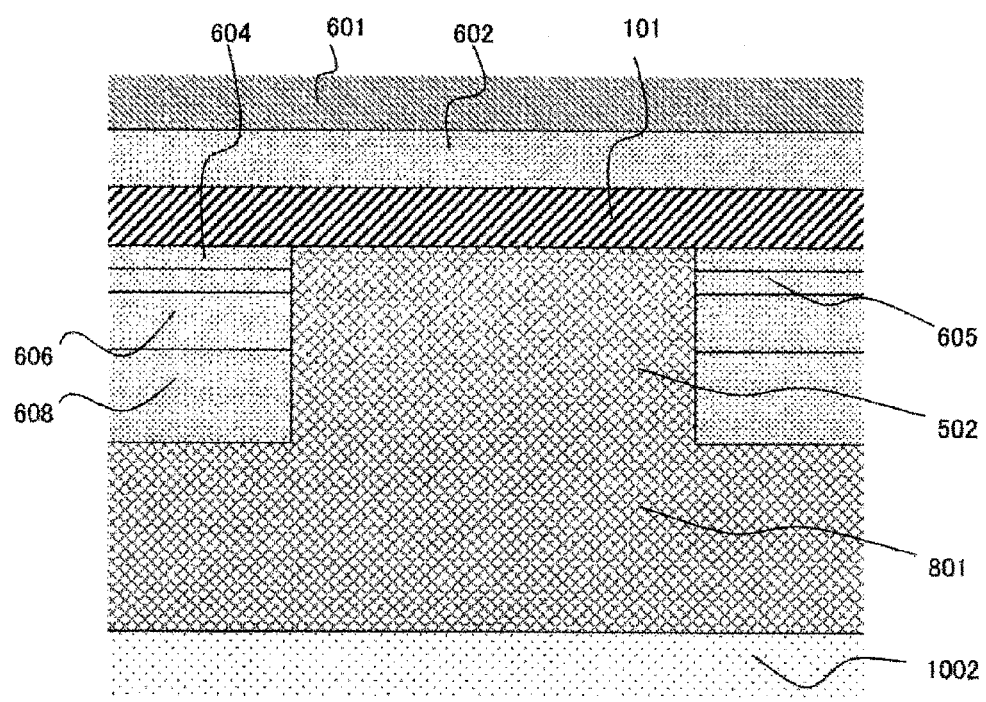

[Fig. 12A]
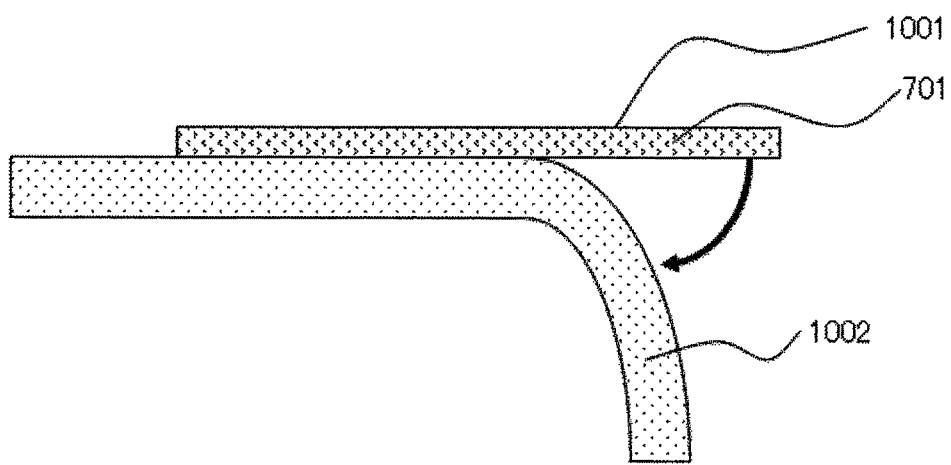

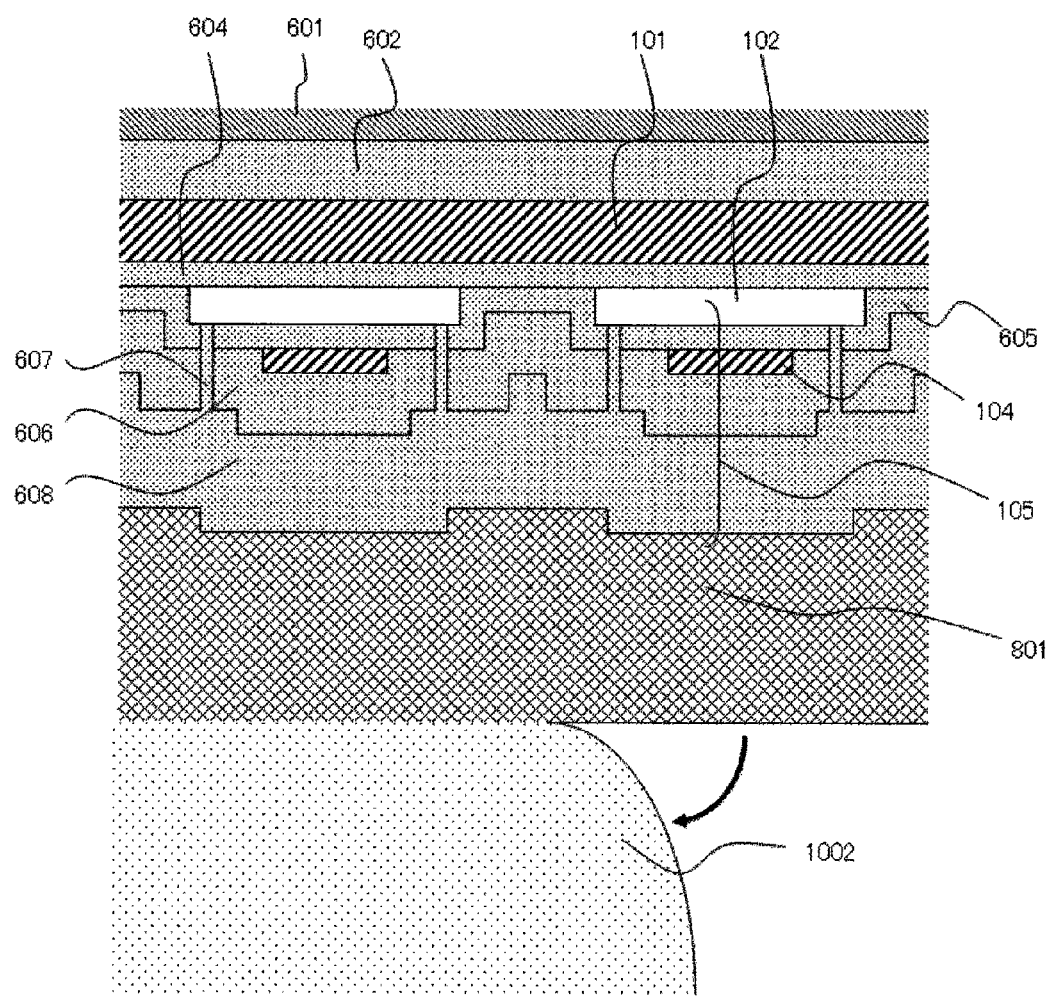
[Fig. 12B]

[Fig. 13A]
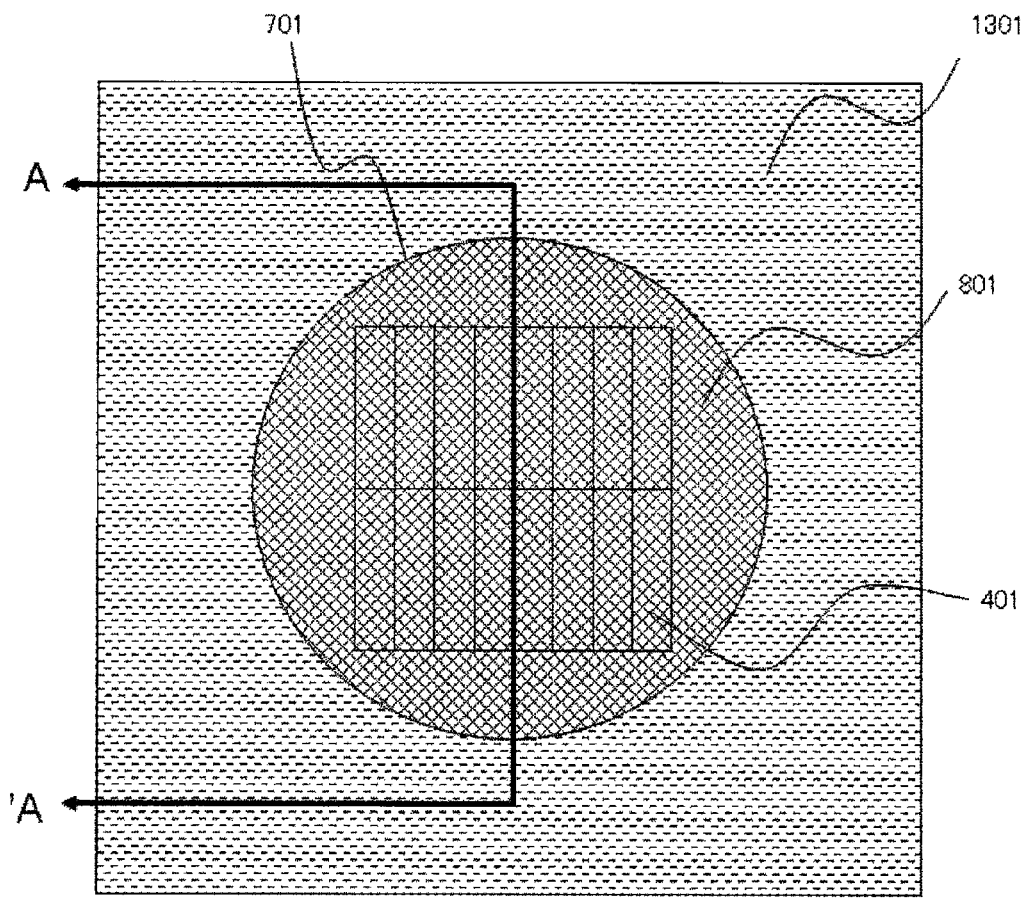
[Fig. 13B]
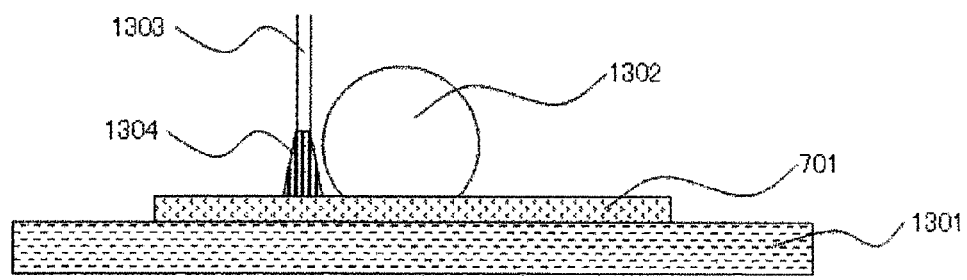

[Fig. 14]
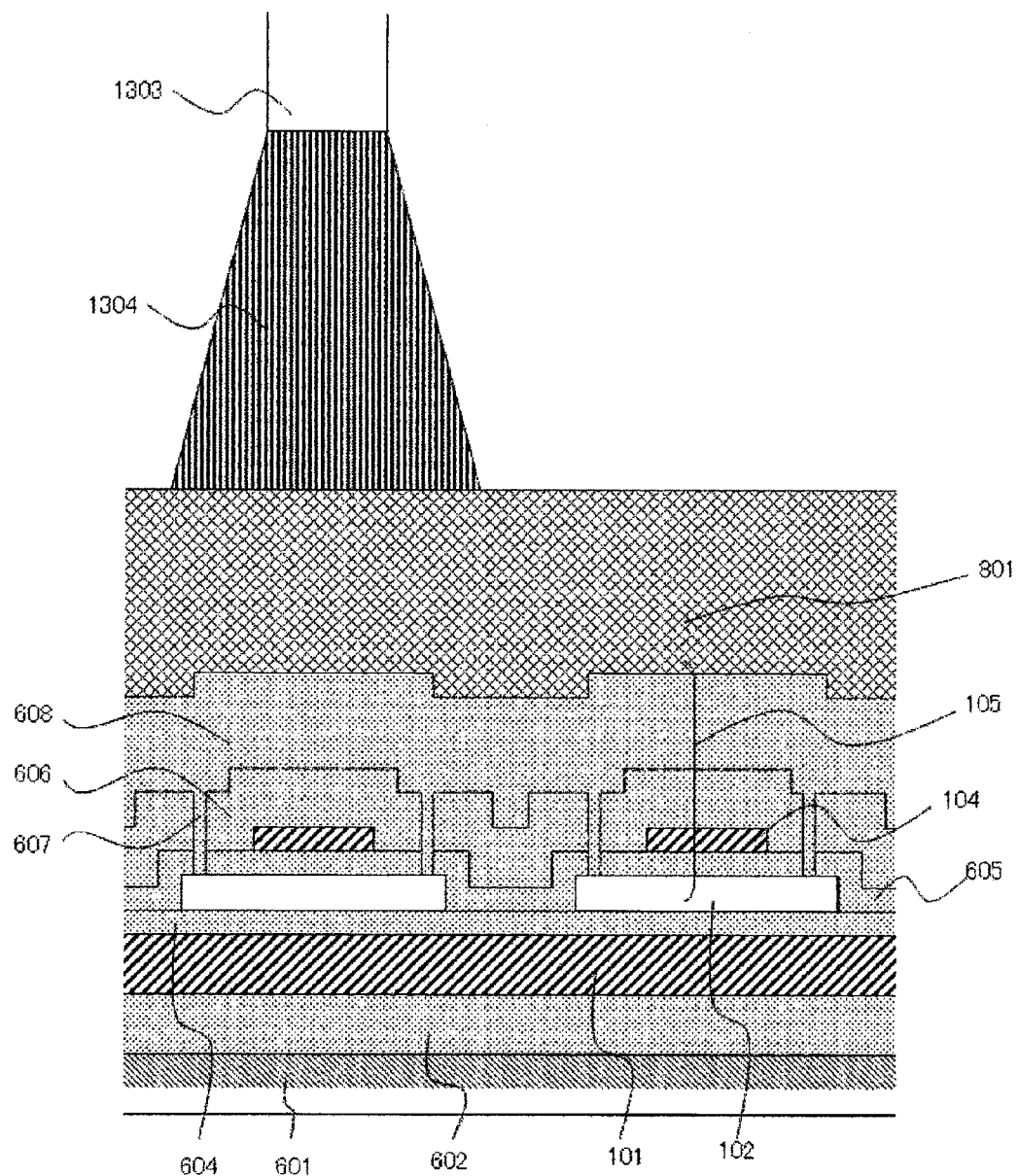

[Fig. 15A]
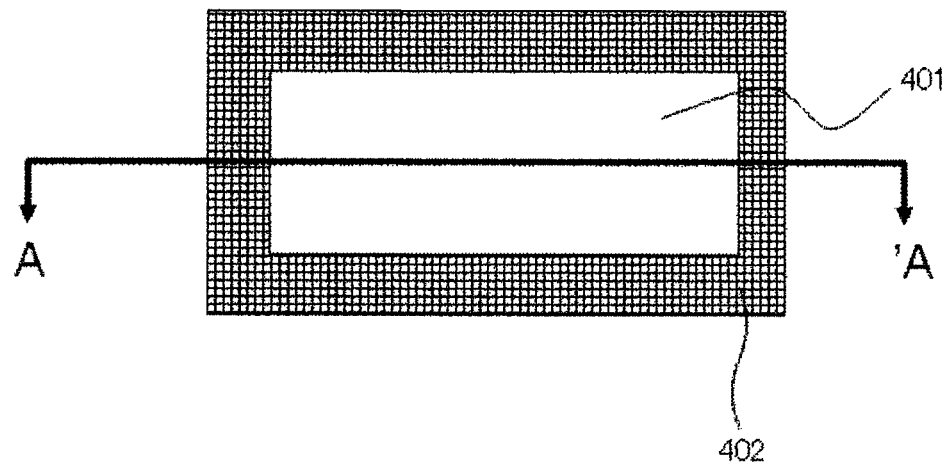
[Fig. 15B]
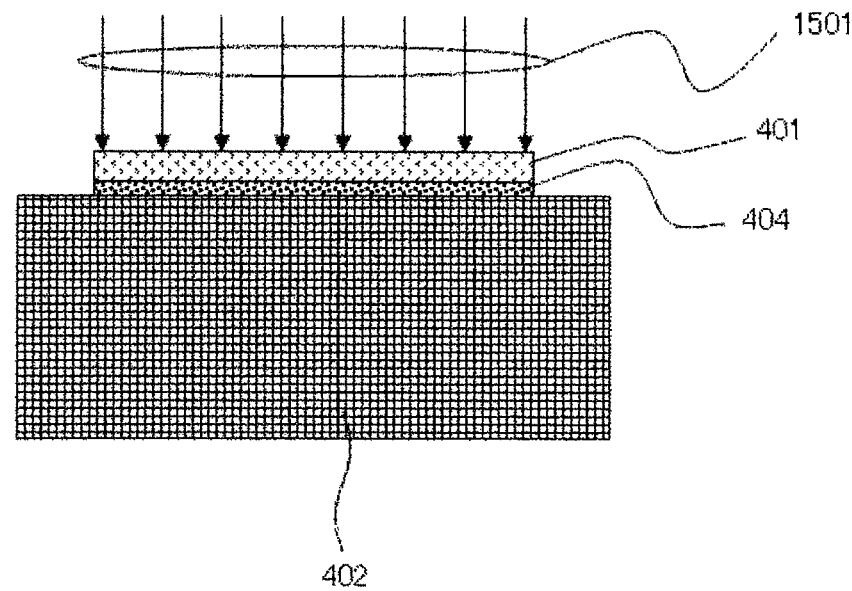

[Fig. 16]
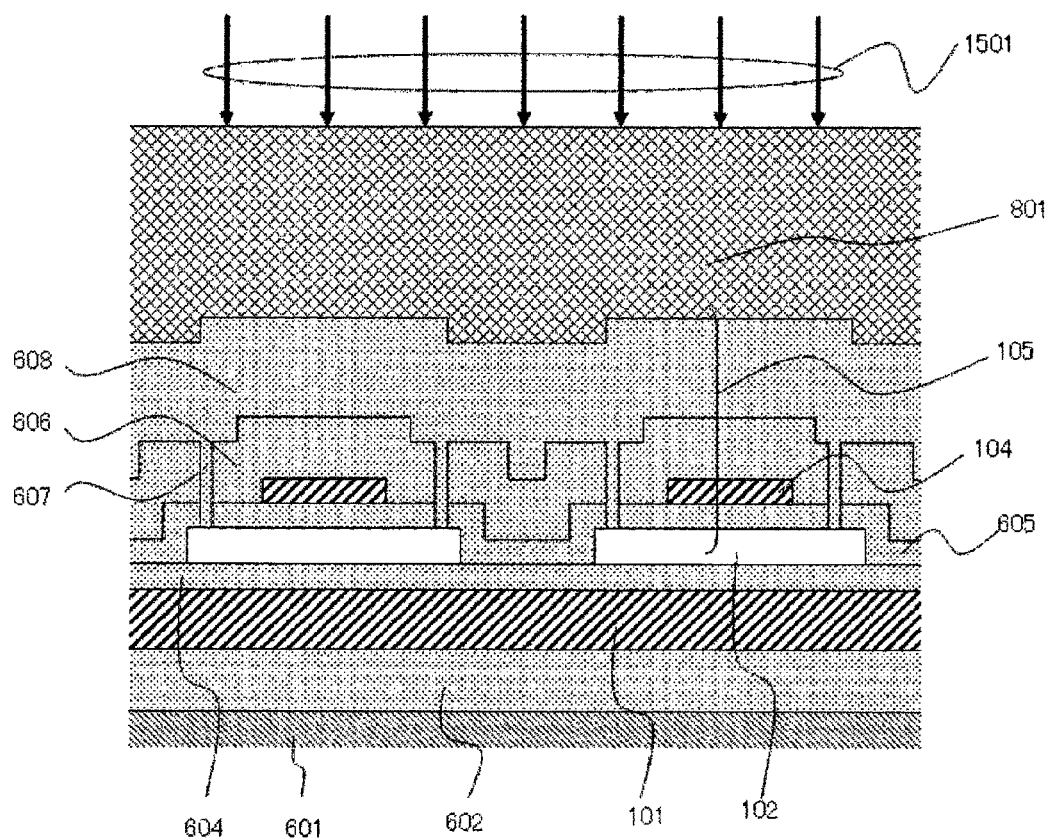

[Fig. 17A]
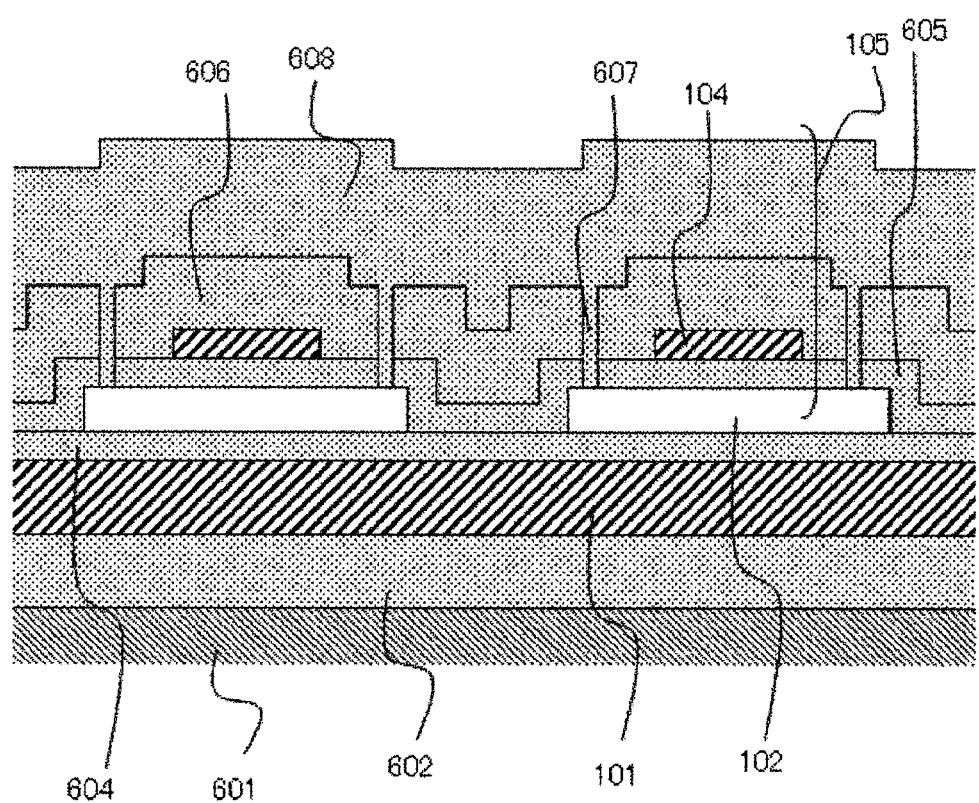

[Fig. 17B]
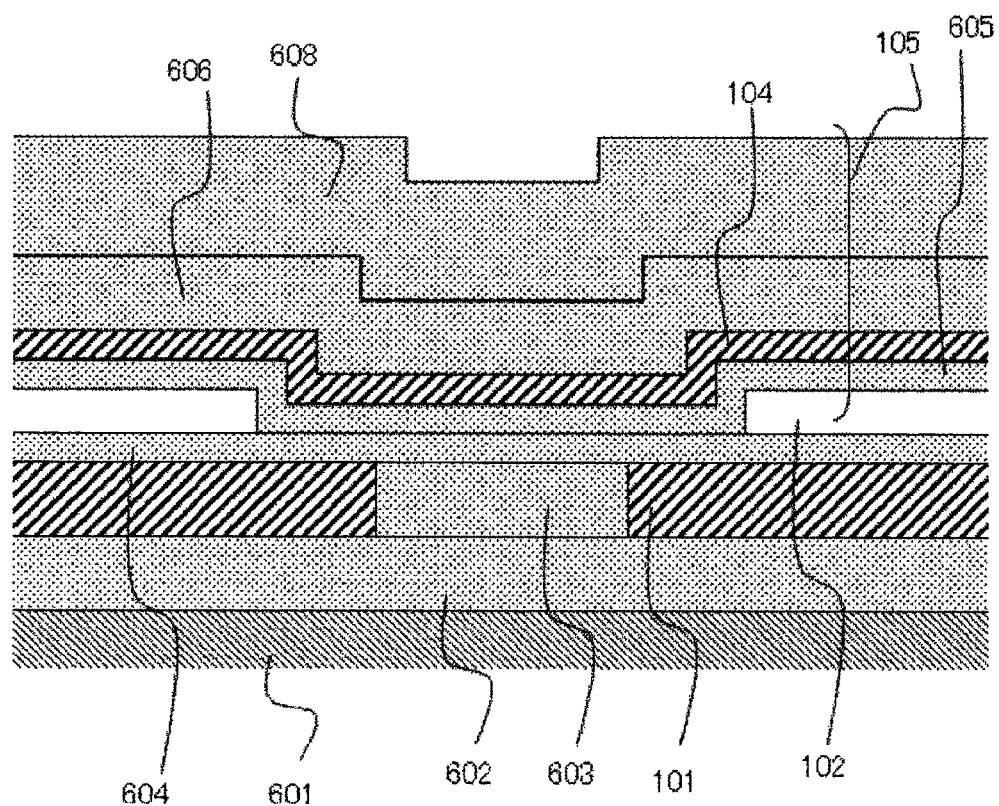

[Fig. 17C]
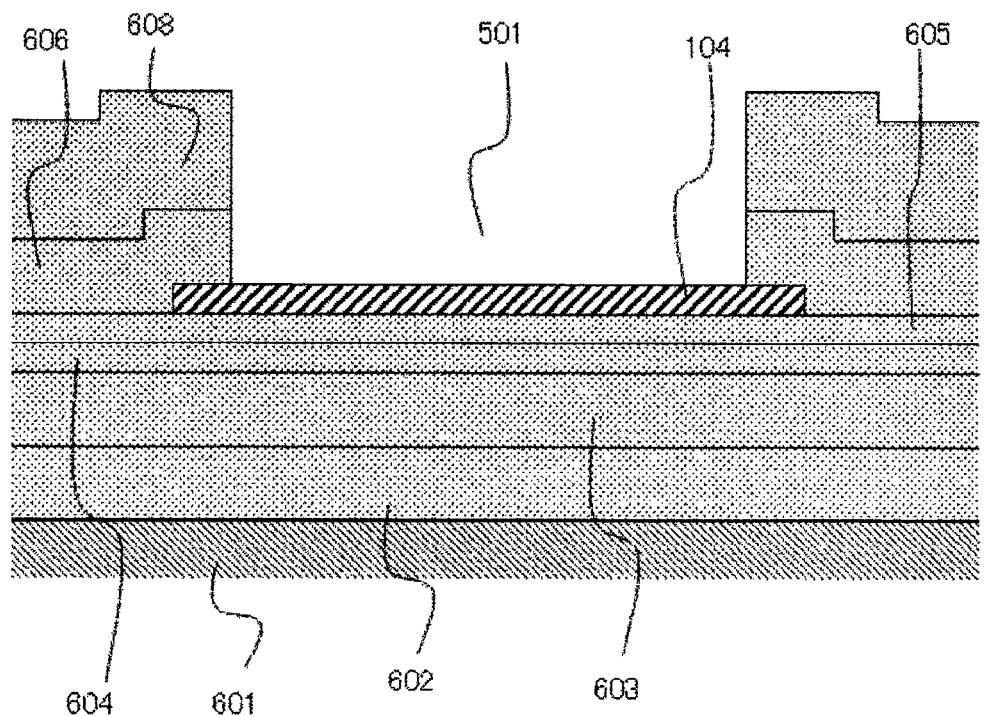
[Fig. 17D]
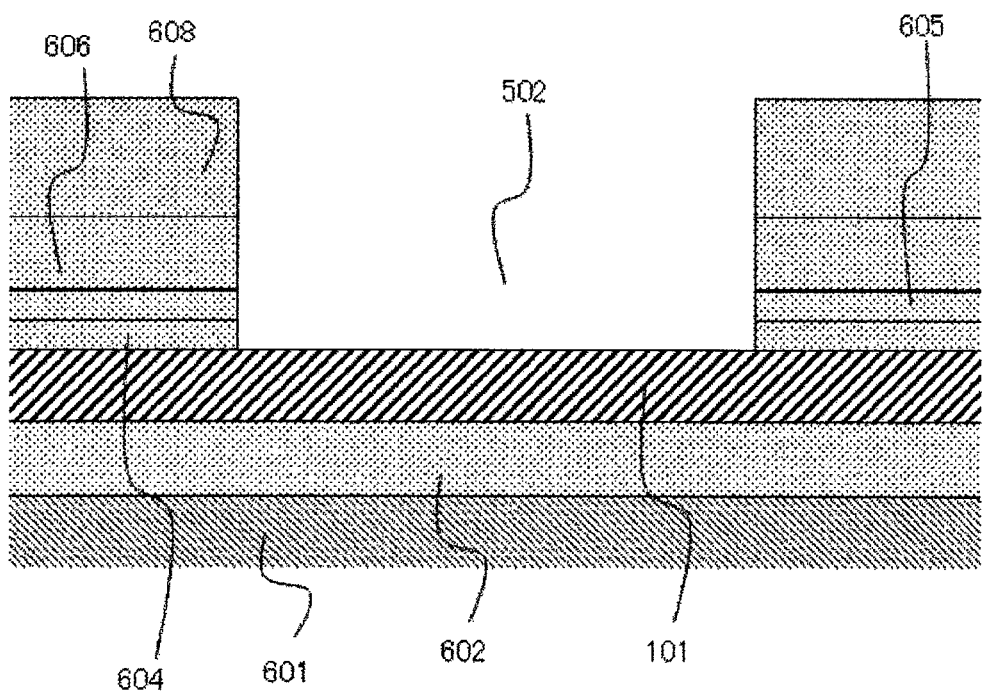

[Fig. 18]
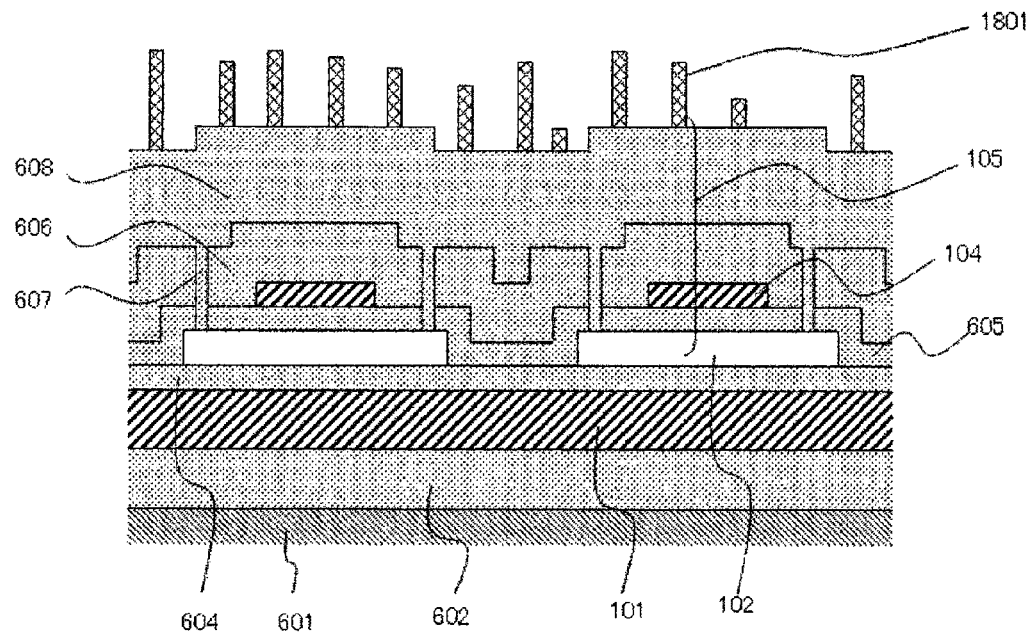
[Fig. 19A]
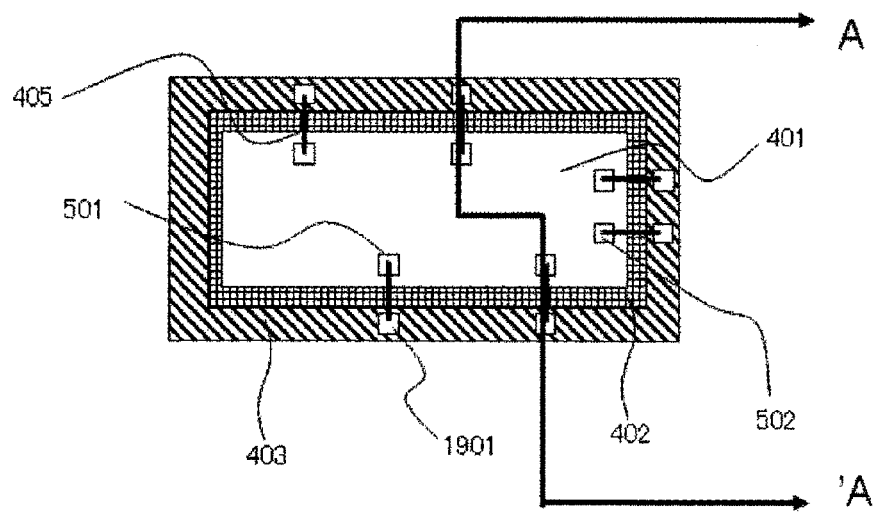

[Fig. 19B]
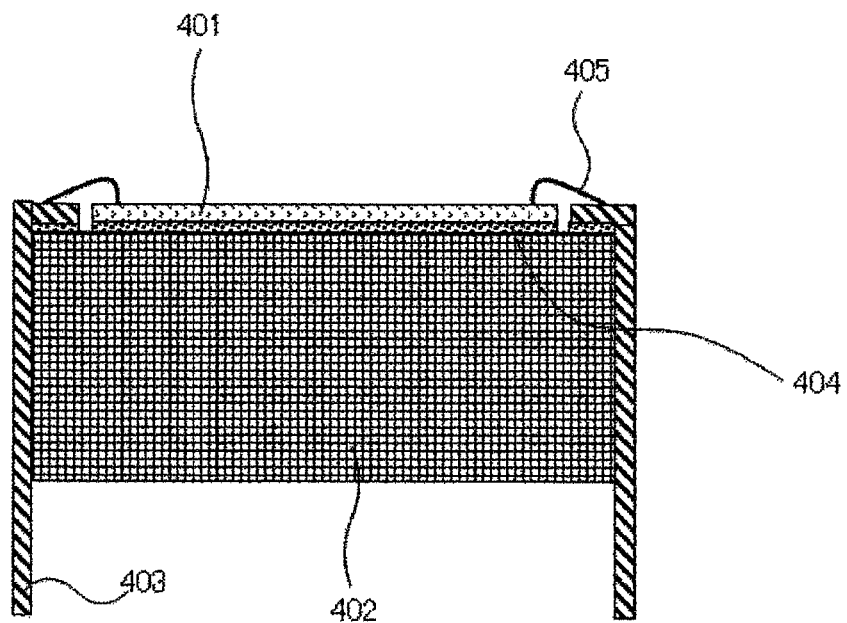

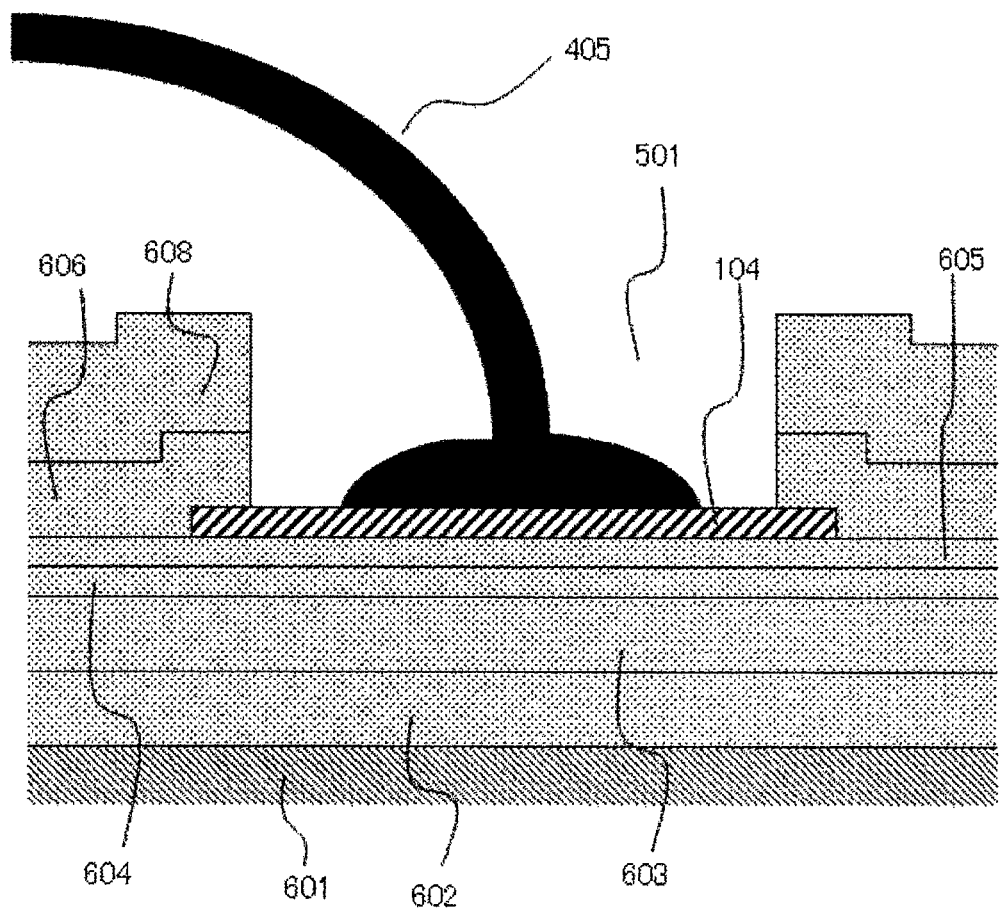
[Fig. 20A]

[Fig. 20B]
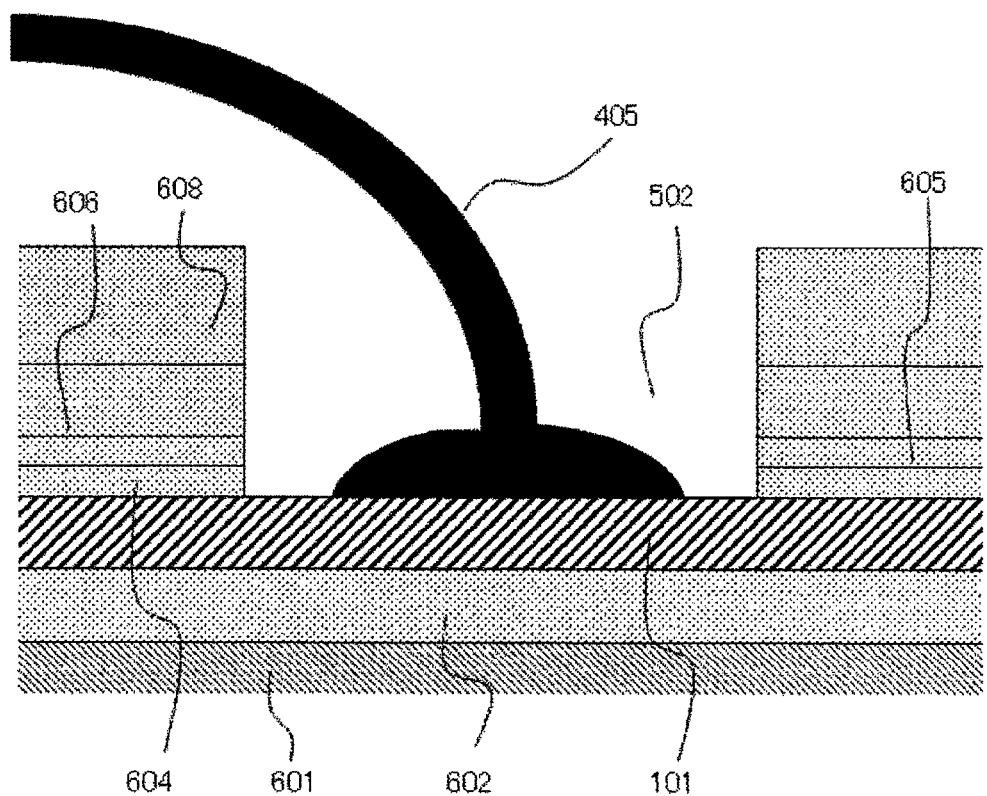
[Fig. 21A]
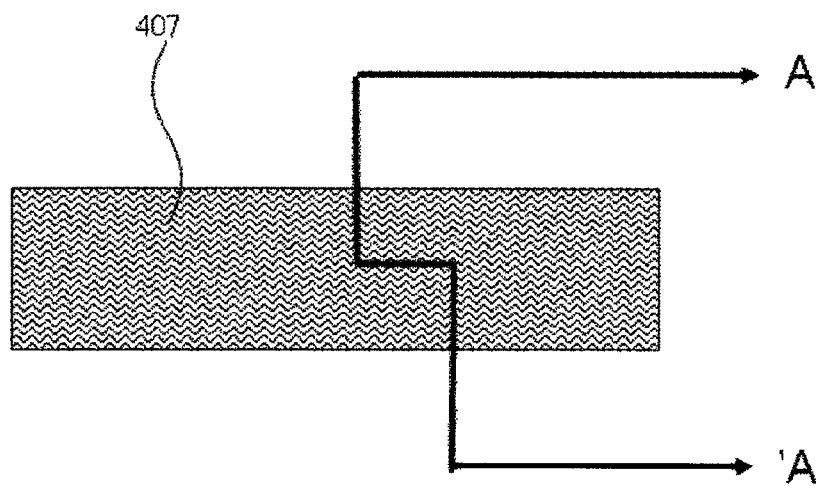

[Fig. 21B]
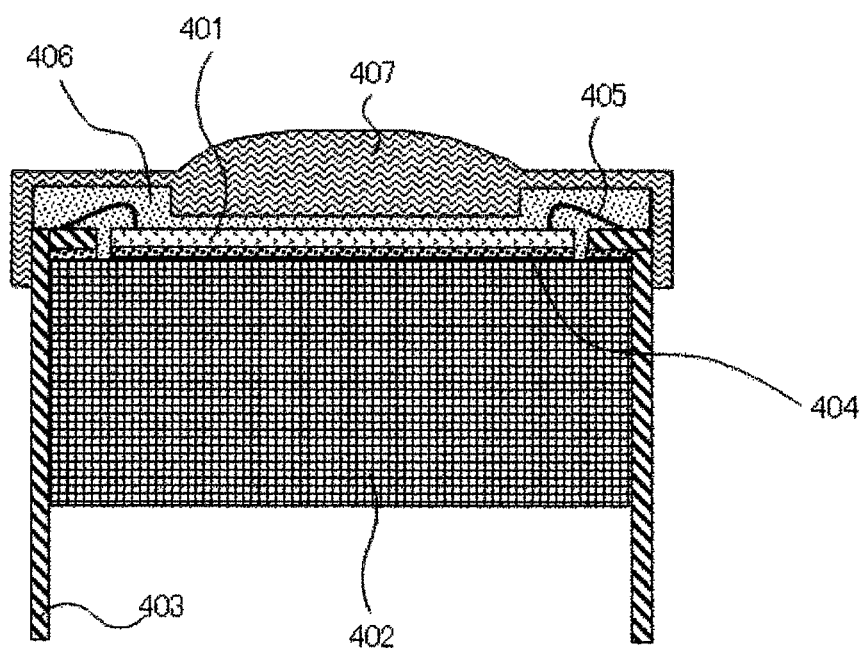

[Fig. 22]
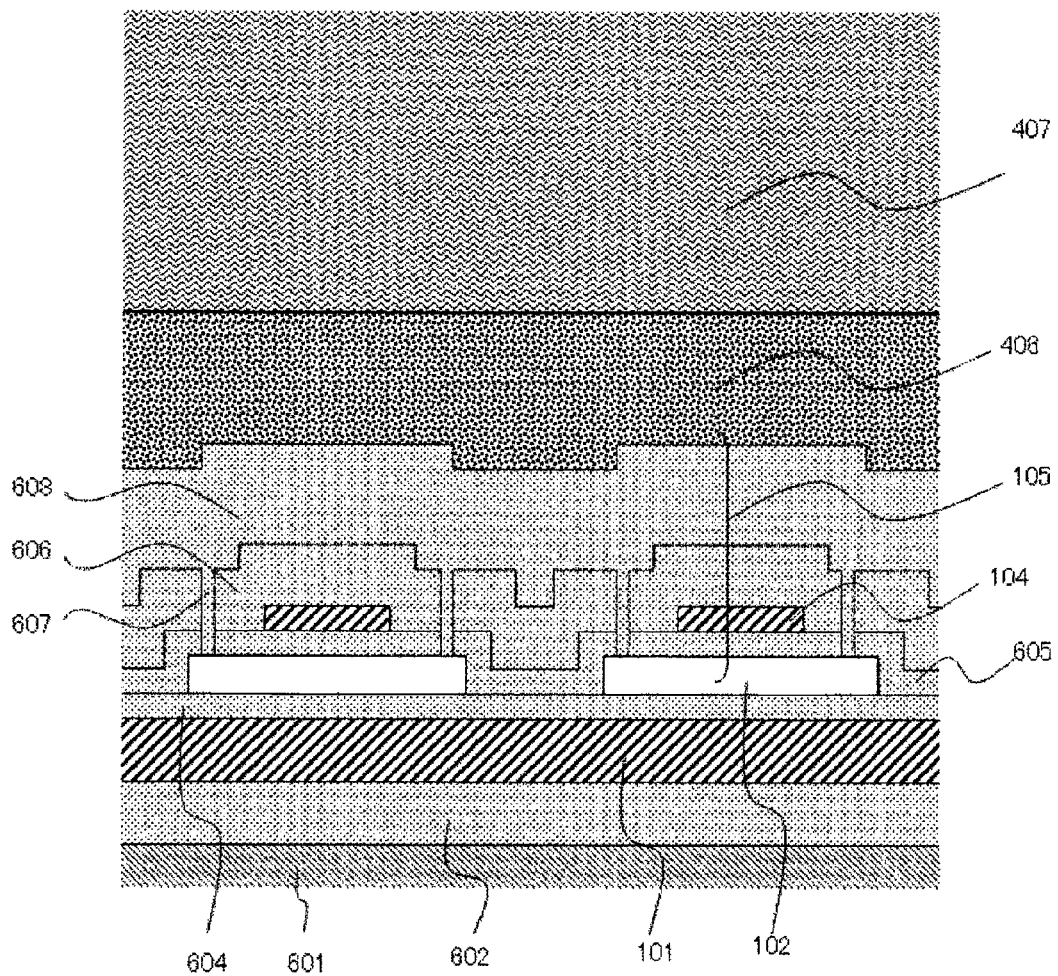

[Fig. 23]
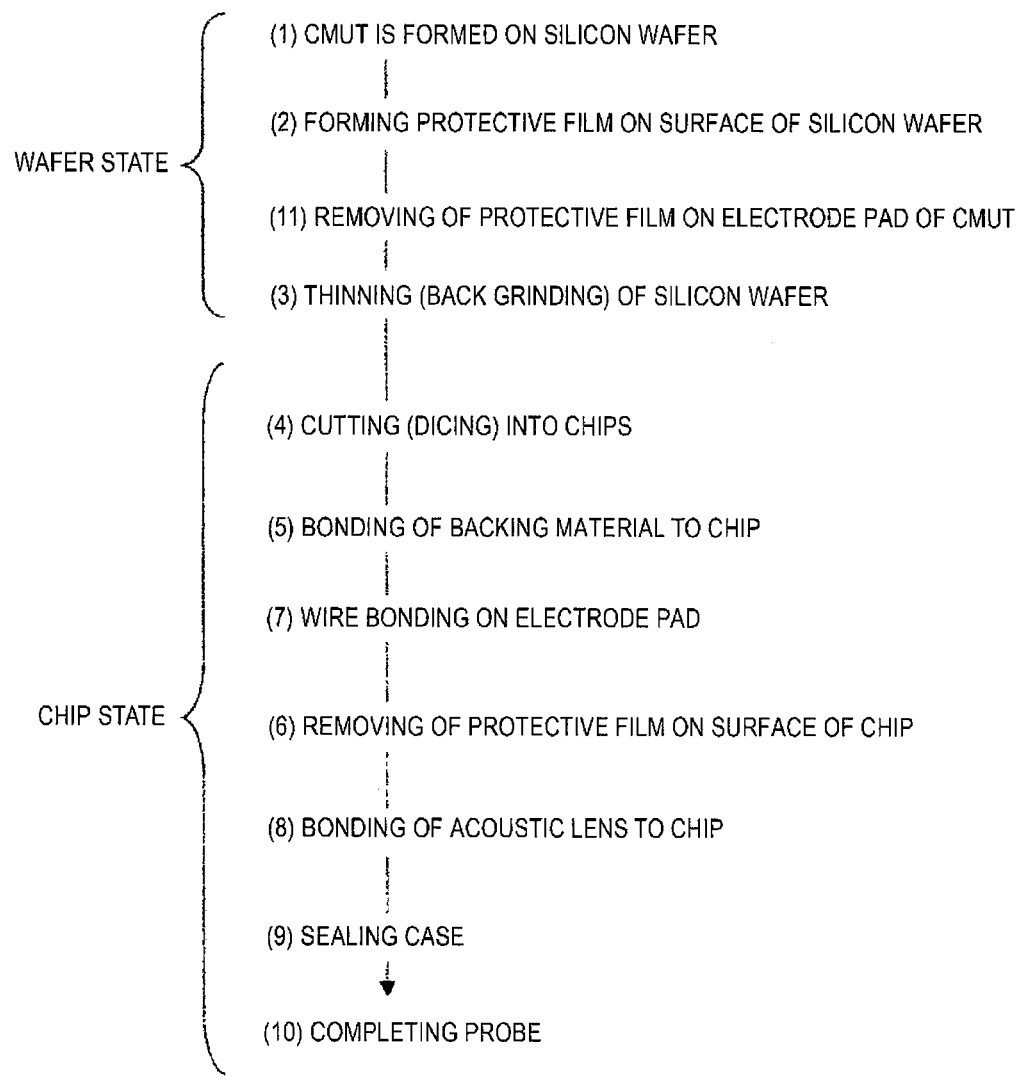

[Fig. 24A]
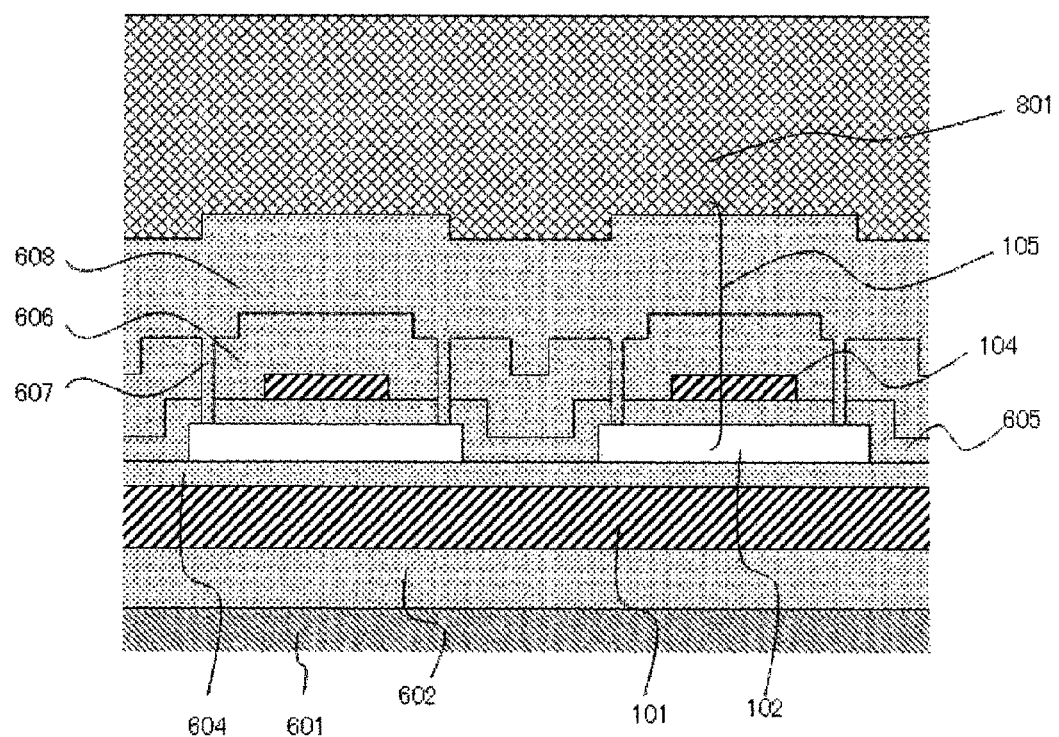

[Fig. 24B]
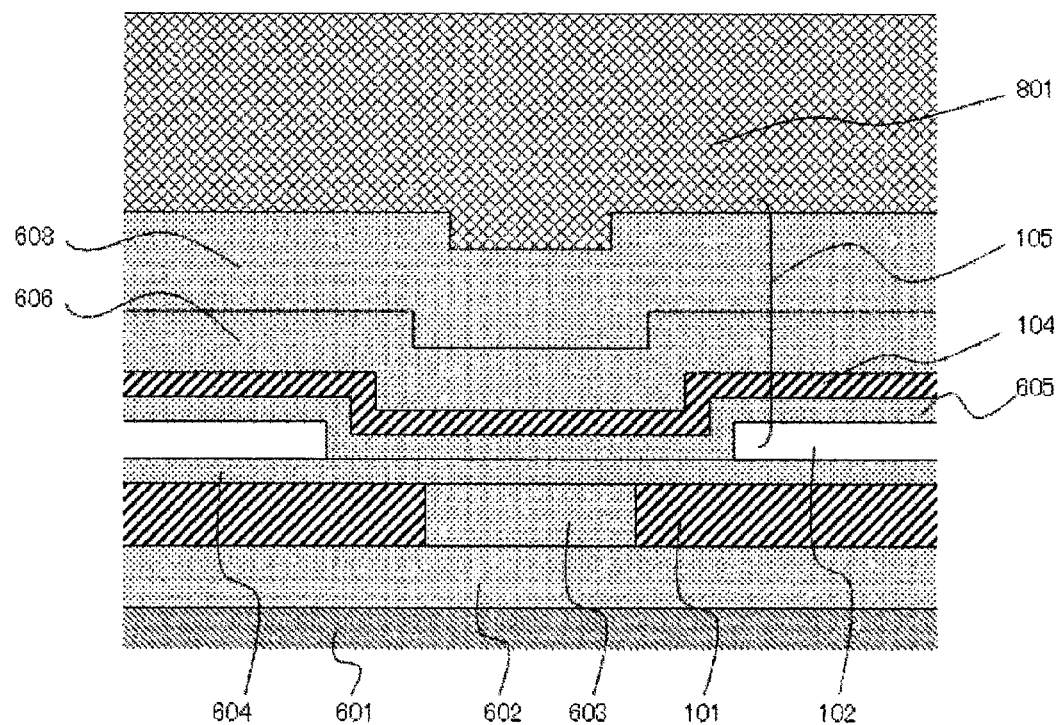

[Fig. 24C]
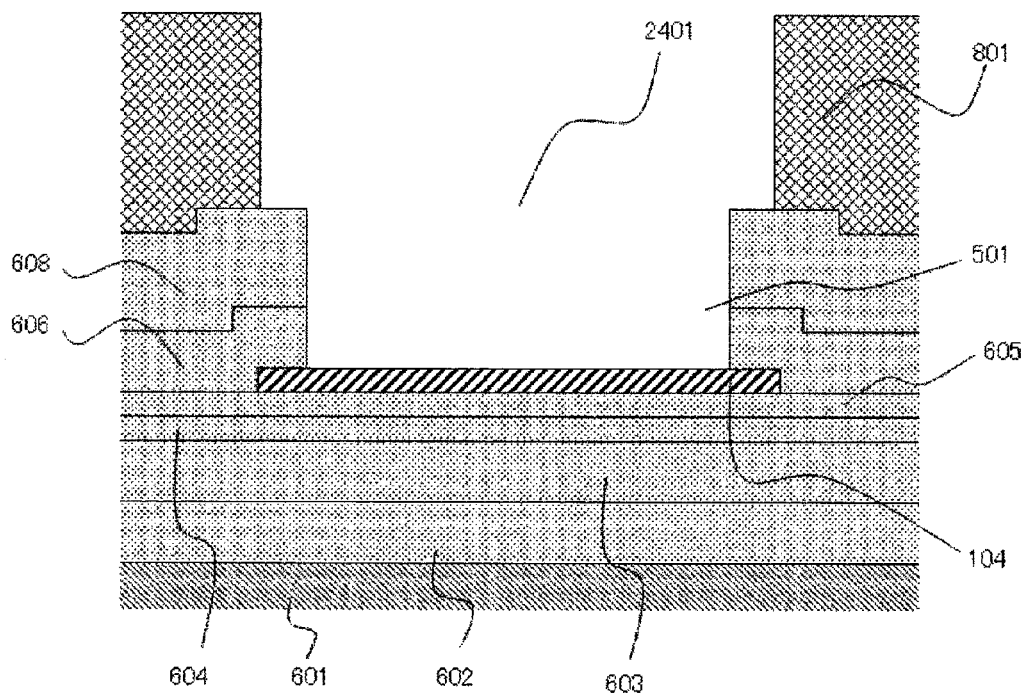

[Fig. 24D]
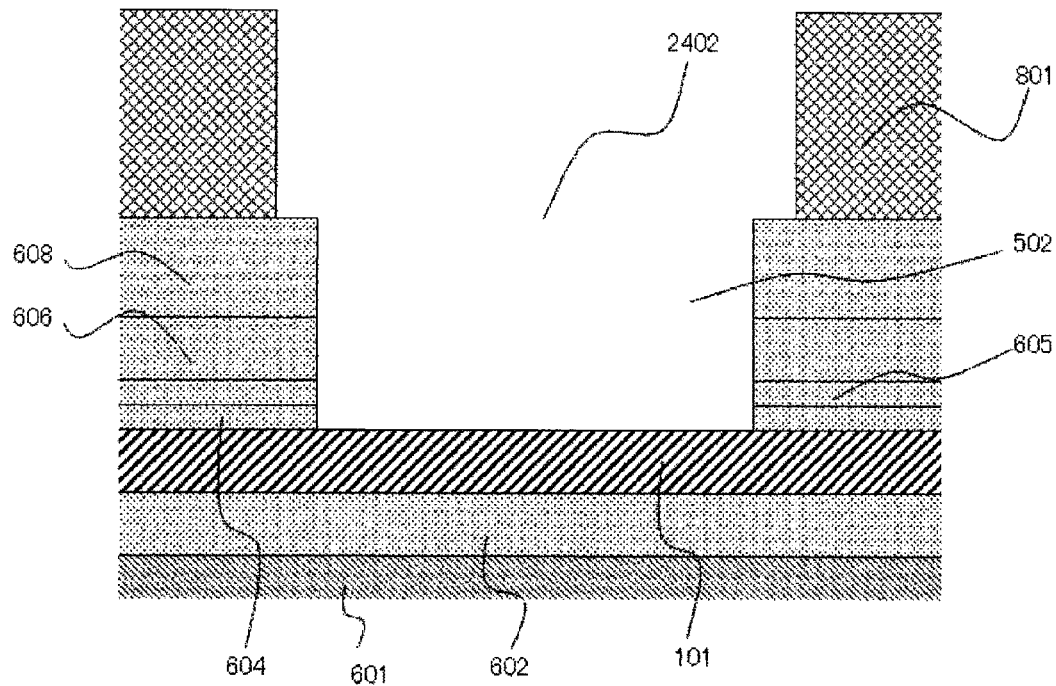

[Fig. 25]
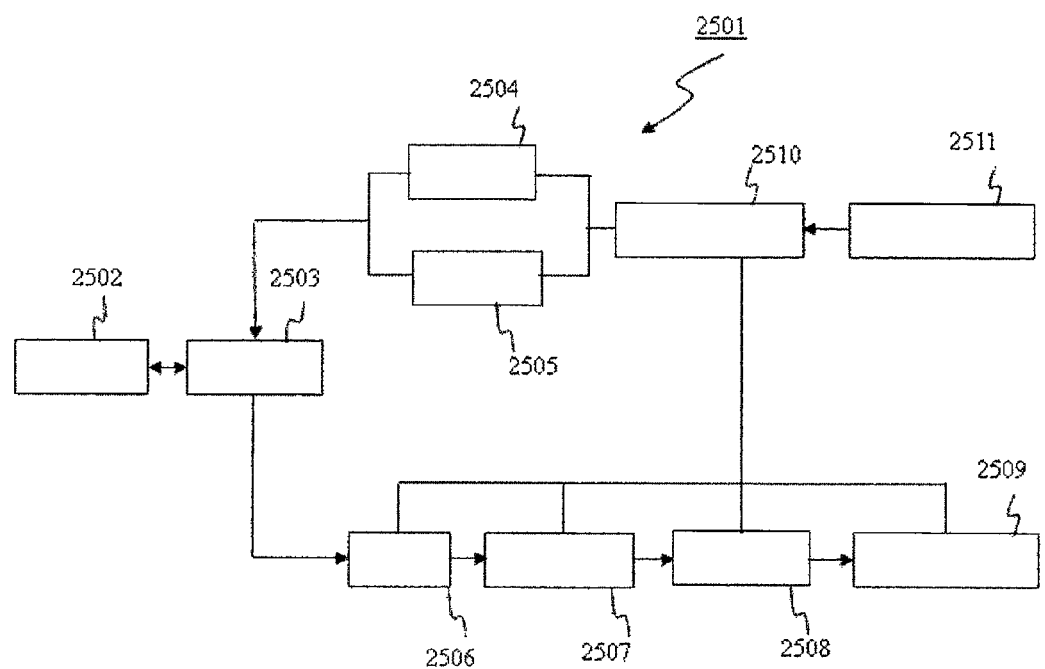

PRODUCTION METHOD FOR ULTRASONIC PROBE, ULTRASONIC PROBE, AND ULTRASONIC DIAGNOSIS DEVICE

TECHNICAL FIELD

The present invention relates to an ultrasonic probe used in an ultrasonic diagnosis device, and in particular, to an optimal technique for producing an ultrasonic transducer used therein.

BACKGROUND ART

An ultrasonic probe using an ultrasonic transducer has been used for diagnosis of a tumor or the like in a human body by transmitting and receiving an ultrasonic wave.

An ultrasonic transducer using vibration of a piezoelectric body has been used. However, a capacitive micromachined ultrasonic transducer (CMUT) in which a vibration unit is manufactured on a silicon wafer has been actively developed for the purpose of practical use, as a result of advances in manufacturing techniques using a recent micro electro mechanical system (MEMS) technique. The CMUT has advantages in terms of a wide frequency band of an ultrasonic wave which can be used, and high sensitivity, compared to the ultrasonic transducer using the piezoelectric body in the related art. In addition, the CMUT is manufactured using an LSI processing technique, and therefore, it is possible to carry out microfabrication. As the related prior arts, there is, for example, PTL 1 or PTL 2 which has been previously filed by the inventor of this specification and relates to a simple structure of an ultrasonic transducer that improves the performance of ultrasonic wave transmission/reception.

CITATION LIST

Patent Literature

PTL 1: JP-T-2001-502871
PTL 2: JP-A-2012-023735

SUMMARY OF INVENTION

Technical Problem

It is considered that the above-described CMUT is essential when independently controlling ultrasonic elements which are arranged in an array. This is because it is considered that while the number of wiring lines in the array becomes great since a wiring line is required for each element, mixed mounting of wiring lines or mixed mounting of a circuit for processing a signal from an ultrasonic transmission/reception unit in one chip is possible in the CMUT.

As a basic structure of the CMUT, a hollow portion which is enclosed by an insulation film is disposed on an upper layer of a lower electrode, and an upper electrode is disposed on the hollow portion via the insulation film. When an AC voltage and a DC voltage are superimposed between the upper electrode and the lower electrode, an ultrasonic wave is transmitted due to vibration of a membrane, which is constituted of the insulation film and the upper electrode on the hollow portion, at an applied frequency of the AC voltage. When the ultrasonic wave is received, the membrane vibrates due to pressure of the ultrasonic wave which has reached the surface of the membrane and the distance between the upper electrode and the lower electrode changes, and thus, the ultrasonic wave is detected as a change in a capacitance.

In a general semiconductor chip, an organic polymer film such as polyimide is formed on the surface of the chip as a buffer layer for protecting the surface of the chip during a dicing step in which the chip is cut out of a semiconductor substrate on which a device is formed, or for suppressing cracking or the like of the chip due to stress of a packaging material when packaging the chip. The same principle also applies to a chip formed with the CMUT.

However, formation of a protective film on the upper layer of the membrane and use of the chip, which is formed with the CMUT, as an ultrasonic probe as it is affect the vibration of the membrane due to an increase in rigidity or mass of the membrane owing to the protective film, or cause plastic deformation of the protective film itself due to repeated vibration of the membrane. Therefore, the acoustic characteristics of the CMUT change from its desired acoustic characteristics while driving the CMUT, and thus, it is impossible to secure operational reliability.

An object of the present invention is to provide a production method for an ultrasonic probe which can suppress damage to a membrane when assembling a chip formed with a CMUT in the ultrasonic probe and can secure operational reliability while driving the CMUT; the ultrasonic probe; and an ultrasonic diagnosis device.

Solution to Problem

In order to achieve the above-described object, the present invention provides a production method for an ultrasonic probe which uses a capacitive ultrasonic transducer formed on a first primary surface of a substrate, including: a step of forming a protective film on the surface of the ultrasonic transducer which is formed on the first primary surface of the substrate; a step of thinning a second primary surface side opposite to the first primary surface of the substrate, after the step of forming a protective film; a step of cutting an ultrasonic transducer chip out of the substrate after the step of thinning; a step of providing a sound absorbing material on the surface of the ultrasonic transducer chip which is opposite to the surface formed with the ultrasonic transducer, after the cutting step; and a first removal step of removing the protective film which is formed on the surface of the ultrasonic transducer, after the step of providing a sound absorbing material.

In addition, in order to achieve the above-described object, there is provided an ultrasonic probe produced through the production method, in which the ultrasonic transducer includes a first electrode; a first insulation film which is formed on the first electrode; a hollow portion which is formed on the first insulation film so as to overlap the first electrode when seen from above; a second insulation film which is formed so as to cover the hollow portion; a second electrode which is formed on the second insulation film so as to overlap the hollow portion when seen from above; and a third insulation film which is formed so as to cover the second electrode. Furthermore, there is also provided an ultrasonic diagnosis device which is provided with the ultrasonic probe and a control unit that controls the ultrasonic probe.

Advantageous Effects of Invention

According to the present invention, it is possible to achieve both controlling the damage to the CMUT when assembling the ultrasonic probe using the chip formed with the CMUT and securing the operational reliability during driving of the CMUT.

BRIEF DESCRIPTION OF DRAWINGS

FIG. 1 is a cross-sectional view of an ultrasonic transducer examined by the present inventors.

FIG. 2 is a view showing an assembly flow of an ultrasonic probe examined by the present inventors.

FIG. 3 is a view of an assembly flow of an ultrasonic probe in Example 1.

FIG. 4A is a top view showing the ultrasonic probe produced through the assembly flow in Example 1.

FIG. 4B is a cross-sectional view taken along line A-A' in FIG. 4A showing the ultrasonic probe produced through the assembly flow in Example 1.

FIG. 5 is a top view of a chip formed with an ultrasonic transducer in Example 1.

FIG. 6A is a cross-sectional view taken along line A-A' of the chip formed with the ultrasonic transducer in FIG. 5.

FIG. 6B is a cross-sectional view taken along line B-B' of the chip formed with the ultrasonic transducer in FIG. 5.

FIG. 6C is a cross-sectional view taken along line C-C' of the chip formed with the ultrasonic transducer in FIG. 5.

FIG. 6D is a cross-sectional view taken along line D-D' of the chip formed with the ultrasonic transducer in FIG. 5.

FIG. 7 is a top view of a silicon wafer on which the chip formed with the ultrasonic transducer shown in FIG. 5 is manufactured.

FIG. 8 is a top view in which a protective film is formed on the surface of the silicon wafer in FIG. 7.

FIG. 9A is a cross-sectional view taken along line A-A' of the ultrasonic transducer in the chip formed with the ultrasonic transducer on the silicon wafer in FIG. 8.

FIG. 9B is a cross-sectional view taken along line B-B' of the ultrasonic transducer in the chip formed with the ultrasonic transducer on the silicon wafer in FIG. 8.

FIG. 9C is a cross-sectional view taken along line C-C' of the ultrasonic transducer in the chip formed with the ultrasonic transducer on the silicon wafer in FIG. 8.

FIG. 9D is a cross-sectional view taken along line D-D' of the ultrasonic transducer in the chip formed with the ultrasonic transducer on the silicon wafer in FIG. 8.

FIG. 10A is a top view of the rear surface of the silicon wafer shown in FIG. 8 when performing thinning by polishing the rear surface using a grinder.

FIG. 10B is a cross-sectional view corresponding to the cross section taken along line A-A' in FIG. 10A.

FIG. 11A is an enlarged cross-sectional view taken along line A-A' on the surface side of the silicon wafer formed with the ultrasonic transducer during the thinning step shown in FIG. 10. (b) corresponds to a cross section taken along line B-B' in FIG. 5, (c) corresponds to a cross section taken along line C-C' in FIG. 5, and (d) corresponds to a cross section taken along line D-D' in FIG. 5.

FIG. 11B is an enlarged cross-sectional view taken along line B-B' on the surface side of the silicon wafer formed with the ultrasonic transducer during the thinning step shown in FIG. 10.

FIG. 11C is an enlarged cross-sectional view taken along line C-C' on the surface side of the silicon wafer formed with the ultrasonic transducer during the thinning step shown in FIG. 10.

FIG. 11D is an enlarged cross-sectional view taken along line D-D' on the surface side of the silicon wafer formed with the ultrasonic transducer during the thinning step shown in FIG. 10.

FIG. 12A is a view showing a state where back grinding tape on the surface of the silicon wafer is being peeled, in the cross section taken along line A-A'.

FIG. 12B is a view showing the state where the back grinding tape on the surface of the silicon wafer is being peeled, in the cross section corresponding to the cross section in FIG. 11A.

FIG. 13A is a top view showing a dicing step in which the chip, which is formed with the ultrasonic transducer, is cut out of the silicon wafer.

FIG. 13B is a view corresponding to the cross section taken along line A-A' in FIG. 13A.

FIG. 14 is an enlarged cross-sectional view, which corresponds to the cross section taken along line A-A' in FIG. 5, on the surface side of the silicon wafer formed with the ultrasonic transducer in FIG. 13B.

FIG. 15A is a top view which shows a step of pasting the chip formed with the ultrasonic transducer on a backing material when seen from the surface side of the chip.

FIG. 15B is a cross-sectional view taken along line A-A' in FIG. 15A.

FIG. 16 is an enlarged cross-sectional view, which corresponds to the cross section taken along line A-A' in FIG. 5, on the surface side of the chip in FIG. 15B.

FIG. 17A is an enlarged cross-sectional view, taken along line A-A' in FIG. 5, on the surface side of the chip formed with the ultrasonic transducer.

FIG. 17B is an enlarged cross-sectional view, taken along line B-B' in FIG. 5, on the surface side of the chip formed with the ultrasonic transducer.

FIG. 17C is an enlarged cross-sectional view, taken along line C-C' in FIG. 5, on the surface side of the chip formed with the ultrasonic transducer.

FIG. 17D is an enlarged cross-sectional view, taken along line D-D' in FIG. 5, on the surface side of the chip formed with the ultrasonic transducer.

FIG. 18 is an enlarged cross-sectional view, which corresponds to the cross section taken along line A-A' in FIG. 5, on the surface side of the chip formed with the ultrasonic transducer on which residue of the protective film remains.

FIG. 19A is a top view when seen from the surface side of a chip of which an electrode pad is subjected to wire bonding.

FIG. 19B is a cross-sectional view, which corresponds to the cross section taken along line A-A' in FIG. 19A, of the chip of which the electrode pad is subjected to wire bonding.

FIG. 20A is a cross-sectional view, which corresponds to the cross section taken along line C-C' in FIG. 5, of a pad opening of the chip shown in FIG. 19.

FIG. 20B is a cross-sectional view, which corresponds to the cross section taken along line D-D' in FIG. 5, of the pad opening of the chip shown in FIG. 19.

FIG. 21A is a top view in which an acoustic lens is mounted on the surface of the chip formed with the ultrasonic transducer.

FIG. 21B is a cross-sectional view taken along line A-A' in FIG. 21A.

FIG. 22 is an enlarged cross-sectional view, which corresponds to the cross section taken along line A-A' in FIG. 5, on the surface side of the chip shown in FIG. 21B.

FIG. 23 is a view of an assembly flow of an ultrasonic probe in Example 2.

FIG. 24A is a view corresponding to the cross section taken along line A-A' in FIG. 5, in a step of (11) in FIG. 23.

FIG. 24B is a view corresponding to the cross section taken along line B-B' in FIG. 5, in a step of (11) in FIG. 23.

FIG. 24C is a view corresponding to the cross section taken along line C-C' in FIG. 5, in a step of (11) in FIG. 23.

FIG. 24D is a view corresponding to the cross section taken along line D-D' in FIG. 5, in a step of (11) in FIG. 23.

FIG. 25 is a view showing a configuration of an ultrasonic diagnosis device using the ultrasonic probes in Examples 1 and 2.

DESCRIPTION OF EMBODIMENTS

Hereinafter, Examples of the present invention will be described in detail based on the drawings. Prior to this, a cross-sectional view of an ultrasonic transducer and an assembly flow of an ultrasonic probe which has been examined by the present inventor will be described using FIGS. 1 and 2.

As a basic structure of the CMUT shown in FIG. 1, a hollow portion 102 which is enclosed by an insulation film 103 is disposed on an upper layer of a lower electrode 101, and an upper electrode 104 is disposed on the hollow portion 102 via the insulation film 103. When an AC voltage and a DC voltage are superimposed between the upper electrode 104 and the lower electrode 101, an electrostatic force is exerted between the upper electrode 104 and the lower electrode 101, and an ultrasonic wave is transmitted due to vibration of a membrane 105, which is constituted of the insulation film 103 and the upper electrode 104 on the hollow portion 102, at an applied frequency of the AC voltage. In contrast, when the ultrasonic wave is received, the membrane 105 vibrates due to pressure of the ultrasonic wave which has reached the surface of the membrane 105. Then, the distance between the upper electrode 104 and the lower electrode 101 changes, and thus, the ultrasonic wave is detected as a change in a capacitance. In this operation principle, the transmission/reception of the ultrasonic wave is performed by deformation of the membrane 105 due to the electrostatic force applied between the upper electrode 104 and the lower electrode 101 and the pressure of the ultrasonic wave which has reached the membrane.

FIG. 2 shows a flow of a step of assembling an ultrasonic probe when using a silicon wafer as a semiconductor substrate forming a CMUT which has been examined by the present inventors. A back grinding step ((2) in FIG. 2) of polishing a rear surface side of the silicon wafer is required in order to realize a chip of which the thickness of the substrate is made thin. Moreover, a dicing step ((3) in FIG. 2) when cutting the chip out of the silicon wafer formed with the CMUT and a mounting step ((4) in FIG. 2) of a backing material on the chip for disposing the backing material on the rear surface of the chip formed with the CMUT, are essential.

In the back grinding step of (2) in FIG. 2, tape called back grinding tape is pasted on a surface side of the silicon wafer; polishing of the rear surface side of the wafer using a grinder, or etching of the rear surface side thereof using gas or liquid is performed, by having the tape as a protective film of the surface of the silicon wafer or a base in the back grinding step. Thereafter, a step of peeling the back grinding tape pasted on the surface of the wafer is required.

At this time, bonding or peeling processing of the back grinding tape on the surface side of the wafer formed with the CMUT is required. However, in a device such as CMUT which has a thin membrane in an upper portion of a hollow structure, a force is exerted on the membrane during the bonding or peeling of the back grinding tape, which causes damage such as cracking or peeling of the membrane.

The dicing step of (3) in FIG. 2 is carried out while spraying water on the surface side of the wafer at a high water pressure in order to remove the scraps during dicing. Therefore, damage to the membrane is inevitable even in the dicing step thereof due to a pressure applied to the membrane on the surface side of the wafer.

In the step of bonding the backing material to the chip, which is formed with the CMUT and is cut through the dicing in (4) in FIG. 2, it is necessary to press the backing material and the chip in order to secure adhesiveness while performing processing of pasting the chip on the backing material through an adhesive agent. At this time, damage to the membrane on the surface side of the chip is inevitable due to pressure applied to the surface side of the chip.

In the embodiment of the present invention described below, the purpose of achieving both controlling the damage to the CMUT caused when assembling the ultrasonic probe and securing the operational reliability during driving of the CMUT is realized by forming a protective film on the surface of the chip formed with the CMUT in the assembly step of the ultrasonic probe, before the step in which damage may occur to the CMUT, and then, by removing the protective film after the step in which damage may occur to the CMUT is finished, during the assembly step of the ultrasonic probe.

In all of the drawings for describing the following Examples, the same members are basically given the same reference numerals, and the description thereof will not be repeated. In addition, in the following Examples, description will be made by being divided into a plurality of sections or Examples when necessary for convenience. However, unless otherwise specified, the divided descriptions are correlated to each other, that is, one is related to a part of or the entirety of the other modification examples, details, supplementary explanation, or the like.

In addition, when the number of elements (including the number, the numerical value, the amount, the range, or the like) is mentioned in the following Examples, the present invention is not limited to the specific number thereof unless otherwise specified or when being obviously limited to the specific number in principle, and the present invention may also include a range greater than or equal to the specified number, or a range less than or equal to the specified number. Furthermore, needless to say, the constituents (including steps of the constituents) in the following Example are not always essential unless otherwise specified or when it is considered as being obviously essential in principle.

Similarly, in the following Example, when the shapes of the constituents or the positional relationships are mentioned, the present invention substantially includes approximate or similar shapes unless otherwise specified or when it is not obviously considered so in principle. The same principle applies to the above-described numerical value or range. Even in a case of a plan view, in some cases, the view is hatched for easy understanding.

EXAMPLE 1

In a production method for an ultrasonic probe, a produced ultrasonic probe, and an ultrasonic diagnosis device using the same, of a first example relate to an example, both controlling damage to a CMUT caused when assembling a chip formed with the CMUT in an ultrasonic probe and securing operational reliability during driving of the CMUT are realized by forming a protective film on a substrate formed with the CMUT before a step of assembling the ultrasonic probe, and then, by removing the protective film after the step in which damage may occur to the membrane of the CMUT is finished, during the step of assembling the ultrasonic probe.

That is, the first example is an example of a production method for an ultrasonic probe which uses a capacitive ultrasonic transducer formed on a first primary surface of a substrate, including: a step of forming a protective film on the surface of the ultrasonic transducer which is formed on the first primary surface of the substrate; a step of thinning a second primary surface side opposite to the first primary surface of the substrate, after the step of forming a protective film; a step of cutting an ultrasonic transducer chip out of the substrate after the step of thinning; a step of providing a sound absorbing material on the surface of the ultrasonic transducer chip which is opposite to the surface formed with the ultrasonic transducer, after the cutting step; and a first removal step of removing the protective film which is formed on the surface of the ultrasonic transducer, after the step of providing a sound absorbing material.

In addition, the first example is an example of an ultrasonic probe produced through the above-described production method for an ultrasonic probe, in which the ultrasonic transducer includes a first electrode; a first insulation film which is formed on the first electrode; a hollow portion which is formed on the first insulation film so as to overlap the first electrode when seen from above; a second insulation film which is formed so as to cover the hollow portion; a second electrode which is formed on the second insulation film so as to overlap the hollow portion when seen from above; and a third insulation film which is formed so as to cover the second electrode. Furthermore, the first example is an example of an ultrasonic diagnosis device which is provided with the ultrasonic probe and a control unit that controls the ultrasonic probe.

FIG. 3 is an assembly flow of the ultrasonic probe in the present example when using a silicon wafer as a substrate forming a CMUT. FIG. 4A is a top view showing the ultrasonic probe which is produced through the assembly flow in FIG. 3 and is completed in (10) of FIG. 3. FIG. 4B is a cross-sectional view showing a cut section along line A-A' in FIG. 4A.

In FIGS. 4A and 4B, 401 is a CMUT chip which is formed with a CMUT; 402 is a backing material; 403 is a flexible wiring substrate for electrical connection with the chip formed with the CMUT; 405 is a wire for electrical connection between the flexible wiring substrate 403 and the chip 401 formed with the CMUT; 407 is an acoustic lens; and 408 is a case of the ultrasonic probe. 404 is an adhesive layer that bonds the chip 401 formed with the CMUT, the flexible wiring substrate, and the backing material to each other; and 406 is an adhesive layer that bonds the chip 401 formed with the CMUT and the acoustic lens 407 to each other.

In the assembly flow in FIG. 3, a protective film is formed ((2) in FIG. 3) on the surface of the silicon wafer formed with the CMUT including the hollow portion. Then, in a back grinding step, thinning of the silicon wafer is performed ((3) in FIG. 3) by grinding the rear surface opposite to the surface of the silicon wafer formed with the protective film. The thinned silicon wafer is cut ((4) in FIG. 3) into chips, each of which is formed with the CMUT through the dicing step. After a step ((5) in FIG. 3) of bonding the cut chip and the backing material, the protective film formed in (2) in FIG. 3 is removed ((6) in FIG. 3). Then, an electrode pad is subjected to wire bonding ((7) in FIG. 3), and the surface of the chip of the CMUT and the acoustic lens are bonded to each other ((8) in FIG. 3), and are then sealed in the case 408 ((9) in FIG. 3) to complete the ultrasonic probe shown in FIG. 4 ((10) in FIG. 3).

FIG. 5 is a top view of the chip 401 formed with the CMUT by the present example and shows a stage of (1) in FIG. 3 in which the CMUT is formed on the silicon wafer. Lower electrodes 101 of two channels and upper electrodes 104 of four channels are orthogonal to each other, and they are in an array structure, in which rectangular hollow portions 102 are arranged at respective intersections, with 100 μm in an arrangement direction of the lower electrode and 40 μm in an arrangement direction of the upper electrode. 501 is a pad opening for electrical connection to the upper electrode and 502 is a pad opening for electrical connection to the lower electrode. The upper electrode 104 and the lower electrode 101 respectively corresponding to the pad openings 501 and 502 become electrode pads. Insulation films are disposed in an upper layer or a lower layer of the lower electrode 101 and an upper layer or a lower layer of the upper electrode 104, but are not shown in FIG. 5.

FIGS. 6A to 6D show cross-sectional structures of the CMUT formed in the chip 401 formed with the CMUT shown in FIG. 5. FIG. 6A corresponds to a cut section along line A-A' in FIG. 5, FIG. 6B corresponds to a cut section along line B-B' in FIG. 5, FIG. 6C corresponds to a cut section along line C-C' in FIG. 5, and FIG. 6D corresponds to a cut section along line D-D' in FIG. 5. In FIGS. 6A to 6D, 601 is a semiconductor substrate and shows a case where the chip is manufactured using an 8-inch silicon wafer in the present example. The thickness of the 8-inch silicon wafer is 725 μm. However, only the vicinity of the CMUT device is shown in FIGS. 6A to 6D.

602, 603, 604, 605, 606, and 608 are insulation films which are formed of, for example, silicon oxide films. As the thicknesses of the insulation films, for example, 602 is 500 nm, 603 is 800 nm, 604 and 605 are 200 nm, 606 is 500 nm, and 608 is 800 nm. 101 is a lower electrode which is formed of, for example, 100 nm of a titanium nitride film, 600 nm of an aluminum alloy film, and 100 nm of a titanium nitride film. 102 is a hollow portion of which the thickness is, for example, 100 nm. 104 is an upper electrode which is formed of, for example, 100 nm of a titanium nitride film, 300 nm of an aluminum alloy film, and 100 nm of a titanium nitride film.

Although not shown in FIG. 5, 607 is an opening for forming the hollow portion 102. The hollow portion 102 is formed through removal of a material which serves as a mold for the hollow portion 102, through the opening 607. After the formation of the hollow portion 102, the opening 607 is embedded with the insulation film 608 to seal the hollow portion 102. 105 is a membrane on the hollow portion. In the present example, the thickness of the membrane is about 2 μm including the thickness of the upper electrode. The above-described thickness, the dimension of the hollow portion, or the material forming the CMUT is merely an example, and is determined in accordance with a desired frequency of an ultrasonic wave or the like which can be transmitted and received. Accordingly, needless to say, in some cases, the membrane on the hollow portion 102 is also made thinner than the above-described example.

FIG. 7 shows a silicon wafer 701 in which a total of 16 chips 401 formed with CMUTs of the present example shown in FIG. 5 are manufactured in an arrangement of 2×8 chips, and corresponds to a state after the step of (1) in FIG.

3. Hereinafter, (2) to (10) of the assembly flow of the ultrasonic probe shown in FIG. 3 will be described using the drawings.

FIGS. 8 and 9 show the step of forming a protective film on the silicon wafer in (2) in FIG. 3. FIG. 8 is a view in which a protective film 801 is formed on the surface of the silicon wafer formed with the chips in FIG. 7, and is an example in which coating type polyimide is used as the protective film. After the surface of the silicon wafer is coated with the protective film 801 formed of polyimide, the coated protective film 801 formed of polyimide is cured through heat treatment performed for 1 hour at 350° C. As the material of the protective film 801, an organic polymer material is preferable, and may also be polybenzoxazole or photoresist or the like which is used in photolithography in a semiconductor process, in addition to polyimide. That is, in the production method for an ultrasonic probe of the present example, a film formed of an organic polymer material is used as the protective film. The organic polymer material has low elasticity, and therefore, has a buffer effect with respect to external force. In addition, the material constituting the CMUT is an inorganic material, and therefore, the protective film is selectively removed during removal of the protective film. Parylene which can be formed through a chemical vapor deposition method may be used for the film in addition to the coating type film.

Each of FIGS. 9A to 9D is a cross-sectional view of the CMUT which is formed on the chip 401 formed with the CMUT on the silicon wafer 701 in FIG. 8. FIG. 9A corresponds to a cut section along line A-A' in FIG. 5, FIG. 9B corresponds to a cut section along line B-B' in FIG. 5, FIG. 9C corresponds to a cut section along line C-C' in FIG. 5, and FIG. 9D corresponds to a cut section along line D-D' in FIG. 5. In FIGS. 9A and 9B, a protective film 801, which is formed of polyimide, is formed with a thickness of 5 μm on an upper layer of the insulation film 608 as an uppermost surface of the CMUT. In FIGS. 9C and 9D, the protective film formed of polyimide is embedded in the upper layer of the insulation film 608 and the pad openings 501 and 502 since the type of the protective film is the coating type.

In this manner, it is possible to suppress damage to the membrane in the back grinding step of (3) for thinning the silicon wafer, in the dicing step of (4) for cutting the chip formed with the CMUT, out of the substrate, and in the step of bonding and pasting the chip formed with the CMUT to the backing material in (5), by performing the step of forming the protective film in (2) between (1) and (3) of FIG. 3. In addition, a usual semiconductor manufacturing apparatus can be used to form the protective film in the state of the silicon wafer, which is beneficial.

Successively to the protective film forming step of (2) in FIG. 3, the step of thinning a silicon wafer in (3) in FIG. 3 is performed. FIGS. 10A and 10B are views in which a back grinding tape 1002 is pasted on the surface of the silicon wafer 701, that is, the surface formed with the CMUT, and thinning is performed by polishing a rear surface 1001 of the silicon wafer, that is, a surface opposite to the surface formed with the CMUT, using a grinder 1003. FIG. 10A is a view of the rear surface 1001 of the silicon wafer when seen from above. The grinder 1003 for polishing is not shown in the drawing in order to show the silicon wafer 701. FIG. 10B is a cut section along line A-A' in FIG. 10A. The silicon wafer with a thickness of 725 μm is thinned up to 200 μm which is a thickness shown by the dotted line in the drawing, using the grinder 1003.

FIGS. 11A to 11D are enlarged cross-sectional views on the surface side of the silicon wafer 701 formed with the CMUT during the thinning step shown in FIGS. 10A and 10B. FIG. 11A corresponds to a cut section along line A-A' in FIG. 5, FIG. 11B corresponds to a cut section along line B-B' in FIG. 5, FIG. 11C corresponds to a cut section along line C-C' in FIG. 5, and FIG. 11D corresponds to a cut section along line D-D' in FIG. 5. In the drawings, the protective film 801 formed of polyimide and the back grinding tape 1002 are closely adhered to each other.

FIGS. 12A and 12B are views in which the thinning is completed through the polishing of the silicon wafer 701 and processing of peeling the back grinding tape 1002 from the surface (surface formed with the CMUT) of the silicon wafer 701 is performed. FIG. 12A corresponds to the cross section in FIG. 10B and FIG. 12B corresponds to the cross section in FIG. 11A. A general method of peeling the back grinding tape is to peel the back grinding tape from the substrate as it is or to peel the back grinding tape while reducing the bonding force of the back grinding tape by irradiating the back grinding tape with ultraviolet rays.

As can be seen from FIG. 10B, the grinder is brought into contact with the rear surface of the silicon wafer 701 during the polishing of the silicon wafer 701 and the grinder is rotated or laterally moved to perform the polishing. That is, a pressure in a thickness direction of the substrate or a frictional force in a horizontal direction of the substrate is applied to the silicon wafer 701. Similarly, equivalent forces are applied between the back grinding tape 1002 and the surface of the silicon wafer 701 which is formed with the CMUT as shown in FIGS. 11A to 11D. Even with a force which does not cause any problems in a usual semiconductor device that does not have the membrane, because the CMUT has the thin membrane, there is a possibility that the membrane may be cracked or peeled off due to the force applied to the surface of the silicon wafer 701. Particularly, there is a concern that when a foreign substance is caught between the back grinding tape 1002 and the silicon wafer 701, a hollow space or a scratch may be generated on the surface of the device due to the foreign substance, which causes cracking or peeling of the membrane.

Similarly, even in processing of peeling the back grinding tape 1002 as shown in FIGS. 12A and 12B, force when peeling the back grinding tape 1002 is applied to the membrane of the CMUT. Even if reducing of a bonding force of the back grinding tape using ultraviolet rays does not cause any problems in a usual semiconductor device that does not have the membrane, because the CMUT has the thin membrane 105, there is a possibility that the membrane 105 may be peeled off or cracked when peeling the back grinding tape 1002.

Even if the generated peeling or cracking is minute, the cracking or peeling becomes significant due to distortion of the membrane caused by vibration of the membrane when the CMUT is actually driven after assembly of the completed chip, which is formed with the CMUT, in an ultrasonic probe. Accordingly, the minute peeling or cracking becomes a fatal defect for the CMUT and degrades the reliability of the ultrasonic probe.

However, in the present example, the protective film 801 is formed on the surface of the silicon wafer 701 which is formed with the CMUT in the stage of (2) in FIG. 3, and therefore, the protective film 801 serves as a buffer layer against the force applied to the surface of the CMUT. For example, although there is a case where the protective film is scratched by a foreign substance, there is no case where the CMUT device is scratched by the foreign substance. As will be described later, the protective film 801 is removed in the middle of the assembly step of the ultrasonic probe.

Therefore, even if the protective film 801 is scratched, this does not affect the reliability of the ultrasonic probe using the CMUT, and therefore, it is possible to secure operational reliability during driving of the CMUT.

Next, successively to the step of (3) in FIG. 3, the step of cutting a chip, which is formed with a CMUT, out of the silicon wafer in (4) in FIG. 3 is performed.

FIGS. 13A and 13B are views in which the step of thinning of the silicon wafer 701 in (3) in FIG. 3 is finished, a dicing tape 1301 is pasted on the rear surface of the silicon wafer 701, that is, a surface opposite to the surface formed with the CMUT, and a chip 401 formed with the CMUT is cut out of the silicon wafer 701.

FIG. 13A is a view of the surface of the silicon wafer, that is, the surface formed with the CMUT, when seen from the above. A dicing blade for dicing, a water ejection nozzle for removing scraps, or the like is not shown in the drawing. FIG. 13B is a cut section along line A-A' in FIG. 13A, in which cutting of the silicon wafer 701 is performed along the outer shape of the chip 401 formed with the CMUT, using the dicing blade 1302. 1303 indicates a high-pressure water ejection nozzle which removes scraps, which are generated through the dicing, by ejecting water 1304 onto the surface of the silicon wafer 701 during the dicing.

FIG. 14 is an enlarged cross-sectional view on the surface side of the silicon wafer 701, which is formed with the CMUT, during the dicing step shown in FIG. 13B and corresponds to the cut section along line A-A' in FIG. 5. In FIG. 14, high pressure water is sprayed onto the surface of the silicon wafer from the nozzle. Even if the pressure of the sprayed water is a pressure which does not cause any problems in a usual semiconductor device that does not have the membrane, because the CMUT has the thin membrane, there is a possibility that the membrane may be cracked or peeled off due to distortion of the membrane caused by the pressure of water sprayed onto the surface of the silicon wafer 701. However, if the pressure of sprayed water is reduced in order to control the problems, it is impossible to remove scraps during the dicing. The scraps remaining on the surface of the CMUT cause scratches or cracking on the chip formed with the CMUT during the step of bonding the chip formed with the CMUT to the backing material in (5) in FIG. 3 which will be described later, and therefore, reliability of the ultrasonic probe which is assembled using the completed CMUT is degraded.

Even if the generated peeling or cracking is minute, the cracking or peeling becomes significant due to distortion of the membrane caused by vibration of the membrane when the CMUT is actually driven after assembly of the completed chip, which is formed with the CMUT, in an ultrasonic probe. Accordingly, the minute peeling or cracking becomes a fatal defect for the CMUT and degrades the reliability of the ultrasonic probe. In addition, the scraps on the surface of the chip formed with the CMUT deteriorate adhesiveness with an acoustic lens which is formed on the surface of the chip formed with the CMUT, and thus, affect an ultrasonic wave which is transmitted to or received from the CMUT.

However, in the present example, the protective film 801 is formed on the surface of the silicon wafer 701 which is formed with the CMUT in the stage of (2) in FIG. 3 and the protective film 801 serves as a buffer layer against the force applied to the surface of the CMUT. Therefore, the pressure of water is not transmitted to the membrane as it is, and it is possible to remove scraps by ejecting water under a pressure which is usually applied to a semiconductor device, and to suppress the generation of cracking or peeling of the membrane to thereby suppress degradation of reliability of the ultrasonic probe using the CMUT.

Next, successively to the cutting step of a chip formed with a CMUT through dicing in (4) in FIG. 3, the step of bonding the backing material to the cut chip which is formed with the CMUT, in (5) in FIG. 3 is performed.

FIGS. 15A and 15B are views showing the step of pasting the cut chip 401, which is formed with the CMUT, on a backing material 402.

FIG. 15A is a view of the surface side of a chip formed with a CMUT when seen from the above, and FIG. 15B is a cut section along line A-A' in FIG. 15A. A backing material is bonded to the rear surface of the chip formed with the CMUT, that is, a surface opposite to the surface formed with the CMUT, through an adhesive layer 404. As an adhesive agent, epoxy resin, a silicon adhesive agent, a die attach film, or the like may be used. 1501 shows a pressure applied to the surface of the chip in order to bond the chip formed with the CMUT and the backing material to each other. For example, when a die attach film is used as the adhesive layer, it is possible to bond the chip to the backing material by adding heat at 150° C. to 180° C. while applying a pressure under about 1 kg/cm 2. The chip formed with a CMUT is closely adhered to the backing material through the pressure. If the adhesiveness is low, a gap is made between the chip formed with the CMUT and the backing material. A component which is released to the rear surface of the chip while an ultrasonic wave is transmitted from the CMUT, or a component which is transmitted through the rear surface of the chip while an ultrasonic wave is received is re-reflected from the gap instead of being transmitted to the backing material, and therefore, acoustic characteristics are remarkably degraded.

FIG. 16 is an enlarged cross-sectional view on the surface side of the chip 401 formed with a CMUT, in the step of pasting the chip formed with a CMUT to the backing material as shown in FIGS. 15A and 15B, and corresponds to the cut section along line A-A' in FIG. 5. In FIG. 16, a pressure 1501 for bonding the chip and the backing material is applied to the surface of the protective film 801, which is formed of polyimide, on the membrane 105 of the CMUT.

In a case where the protective film 801 is not formed, there is a possibility that cracking or peeling of the membrane may be caused due to distortion of the thin membrane which is caused by the applied pressure. Particularly, when there is a foreign substance on the surface of the membrane of the CMUT, the foreign substance is directly pressed to the membrane of the CMUT, which causes peeling or cracking of the membrane. Even if the generated peeling or cracking is minute, the cracking or peeling becomes significant due to distortion of the membrane caused by vibration of the membrane when the CMUT is actually driven after assembly of the completed chip, which is formed with the CMUT, in an ultrasonic probe. Accordingly, the minute peeling or cracking becomes a fatal defect for the CMUT and degrades the reliability of the ultrasonic probe.

However, in the present example, the protective film 801 is formed on the surface of the chip which is formed with a CMUT in the stage of (2) in FIG. 3, and therefore, the protective film 801 serves as a buffer layer against the force applied to the surface of the CMUT. For example, although there is a case where the protective film is scratched by a foreign substance, there is no case where the CMUT device is scratched by the foreign substance. As will be described later, the protective film 801 is removed in the middle of the assembly step of the ultrasonic probe. Therefore, even if the protective film 801 is scratched, this does not affect the reliability of the ultrasonic probe using the CMUT, and therefore, it is possible to secure the operational reliability during driving of the CMUT.

Next, in the present example, successively to the step of pasting the chip formed with a CMUT to the backing material in (5) in FIG. 3, the first removal step of removing the protective film on the surface of the chip formed with the CMUT including a hollow portion, in (6) in FIG. 3 is performed. In the first removal step, it is necessary to remove the protective film overlapping the hollow portion when seen from above, in the protective film on the surface formed with the CMUT.

FIGS. 17A to 17D are enlarged cross-sectional views on the surface side of the chip 401 formed with a CMUT in which a protective film formed of polyimide is removed after the backing material is bonded to the rear surface of the chip formed with the CMUT. FIG. 17A corresponds to a cut section along line A-A' in FIG. 5, FIG. 17B corresponds to a cut section along line B-B' in FIG. 5, FIG. 17C corresponds to a cut section along line C-C' in FIG. 5, and FIG. 17D corresponds to a cut section along line D-D' in FIG. 5. The configuration of FIG. 17 is the same as that of FIG. 6 in that the protective film is removed, but in FIG. 17, the backing material is mounted on the rear surface of the chip formed with the CMUT through an adhesive agent.

In the present example, there is no step of exerting a direct force on the surface of the chip formed with a CMUT and causing damage to the membrane of the CMUT, after the step of (5) in the assembly flow of an ultrasonic probe using the CMUT as shown in FIG. 3, and therefore, the protective film is removed in this stage. Characteristic variation during driving of the CMUT which is caused by an influence of an increase in rigidity or mass of the membrane on vibration of the membrane, or by plastic deformation of the protective film itself due to repeated vibration of the membrane is suppressed through the steps, and thus, it is possible to secure operational reliability of the device during the driving of the CMUT.

In addition, as shown in FIGS. 17C and 17D, protective films on the pad opening 501 for electrical connection to the upper electrode and on the pad opening 502 for electrical connection to the lower electrode are removed, and therefore, electrode pads can be subjected to wire bonding as in (7) in FIG. 3. The protective films can be removed by performing dry etching processing using oxygen plasma when polyimide or other organic polymer materials are used as the protective films. In a case of etching processing using oxygen plasma in which the material constituting the CMUT is an inorganic material, the membrane of the CMUT or other portions are not etched and the protective films can be selectively removed, and therefore, the processing does not affect the characteristics of the CMUT.

As another method of removing a protective film, when polyimide or other organic polymer materials are used, it is possible to remove the protective film by performing wet etching using a removing liquid such as hydrazine. In addition, in some cases, a silane coupling agent is mixed with polyimide-based resin which is used as a protective film of a usual semiconductor chip. Therefore, in some cases, in the processing using oxygen plasma, residue 1801 of the protective film remains as shown in FIG. 18. However, if the protective film is divided and the divided protective film is completely removed up to the surface of the insulation film 608, an influence on the vibration of the membrane due to an increase in rigidity or mass of the membrane, or an influence on plastic deformation of the protective film itself due to repeated vibration of the membrane is small, and the same effect can be obtained.

Next, successively to the first removal step of removing a protective film on the surface of a chip formed with a CMUT in (6) in FIG. 3, the wire bonding step of (7) in FIG. 3 is performed on the electrode pad.

FIGS. 19A and 19B are views in which the electrode pad of the chip formed with a CMUT has been subjected to wire bonding. FIG. 19A is a top view when seen from the surface side of a chip 401 formed with a CMUT. FIG. 19B shows a cut section along line A-A' in FIG. 19A. Similarly to the method of pasting the chip formed with the CMUT on the backing material, the flexible wiring substrate 403 is pasted on the backing material 402 through an adhesive agent, and pad openings 501 and 502 which become electrode pads of the CMUT are connected to an electrode pad 1901 of the flexible wiring substrate 403 through a wire.

FIGS. 20A and 20B are cross-sectional views of the pad openings of the electrode pads of the chip formed with a CMUT. FIG. 20A is a cross-sectional view corresponding to across section taken along line C-C' in FIG. 5 and FIG. 20B is a cross-sectional view corresponding to a cross section taken along line D-D' in FIG. 5. Since the removal of the protective film is performed before the wire bonding step, the protective film on the pad openings 501 and 502 is removed, and therefore, wire bonding is made possible.

Next, the process of pasting an acoustic lens on a chip in (8) in FIG. 3 is performed.

FIG. 21A is a top view in which an acoustic lens is mounted on the surface of the chip 401 formed with a CMUT. FIG. 21B is a cross-sectional view taken along line A-A' in FIG. 21A. An acoustic lens 407 is bonded to the chip 401 formed with a CMUT through an adhesive layer 406. FIG. 22 is an enlarged cross-sectional view on the surface side of the chip 401 formed with a CMUT and corresponds to the cross section taken along line A-A' in FIG. 5. As the material of the adhesive layer, a material similar to the acoustic lens is desirable, and for example, when silicone rubber is used as the acoustic lens, it is desirable that the adhesive layer is also a silicone adhesive agent.

Finally, a case 408 of which the cross-sectional view is shown in FIG. 4B is mounted to complete an ultrasonic probe.

In this manner, according to the present example, the number of steps of directly applying force on the surface of the chip formed with a CMUT is up to (5) in FIG. 3. Therefore, it is possible to remove the protective film before wire bonding. In addition, the protective film on the electrode pad of the chip is also removed together, and therefore, the step is simplified. Furthermore, it is possible to eliminate damage, such as a flexible substrate being etched and wiring lines on the substrate being melted, which the flexible substrate or the like connected to the electrode pad of the chip through bonding wires, through oxygen plasma processing, wet etching processing, or the like which is a process of removing the protective film.

As described above, in the production method for an ultrasonic probe of the present example, with the formation of the protective film before performing thinning processing of the silicon wafer formed with a CMUT, it is possible to suppress damage to the membrane of the CMUT, in particular, cracking or peeling of the membrane of the CMUT, which is caused in the successive steps of thinning of the silicon wafer, cutting of a chip, which is formed with the CMUT, out of the silicon wafer, and pasting the chip formed with the CMUT on a backing material. In addition, with the removal of the protective film before the wire bonding step performed on the chip formed with the CMUT, it is possible to easily perform the wire bonding, and in the assembled ultrasonic probe, it is possible to suppress an influence on the vibration of the membrane due to an increase in rigidity or mass of the membrane of the CMUT, or an influence on plastic deformation of the protective film itself due to repeated vibration of the membrane, and to achieve both controlling damage to the CMUT and securing operational reliability during driving of the CMUT.

The planar shape of a CMUT cell is a rectangular shape in FIG. 5, but the shape is not limited thereto. For example, the shape may be a polygonal shape or a circular shape as disclosed in PTL 2. In addition, the material constituting the CMUT or the ultrasonic probe, or the thickness of each of the members shown in the present example indicates one of the combinations thereof. For example, in regard to the lower electrode, a semiconductor substrate may be favorable or, as shown in FIG. 5, a conductive film on an insulation film formed on a semiconductor substrate, or a conductive film on a semiconductor substrate which is formed with a signal processing circuit may be also favorable. Furthermore, an array configuration with two channels for the lower electrode and four channels for the upper electrode is shown in FIG. 5. However, needless to say, the configuration may not be the array configuration, or may be an array configuration with a larger number of channels.

EXAMPLE 2

Next, a production method for an ultrasonic probe of a second example will be described using FIGS. 23 to 24D. In the above-described Example 1, the step of forming a protective film in (2) in FIG. 3 is performed between the step of forming a CMUT on a silicon wafer in (1) and the step of thinning the silicon wafer in (3), and the first removal step of removing the protective film in (6) is performed between the step of bonding a chip formed with the CMUT to a backing material in (5) and the wire bonding step which is performed on an electrode pad in (7). However, Example 2 is a production method for an ultrasonic probe in which a second removal step of removing the protective film on the electrode pad of the CMUT as (11) is performed between the formation of the protective film (2) and the thinning of the silicon wafer in (3), as shown in FIG. 23.

That is, the second example relates to a production method for an ultrasonic probe which uses a capacitive ultrasonic transducer formed on a first primary surface of a substrate, including: a step of forming a protective film on the surface of the ultrasonic transducer which is formed on the first primary surface of the substrate; a step of thinning a second primary surface side opposite to the first primary surface of the substrate, after the step of forming a protective film; a step of cutting an ultrasonic transducer chip out of the substrate after the step of thinning; a step of providing a sound absorbing material on the surface of the ultrasonic transducer chip which is opposite to the surface formed with the ultrasonic transducer, after the cutting step; and a first removal step of removing the protective film which is formed on the surface of the ultrasonic transducer, after the step of providing a sound absorbing material. Furthermore, the above-described ultrasonic transducer includes a first electrode; a first insulation film which is formed on the first electrode; a hollow portion which is formed on the first insulation film so as to overlap the first electrode when seen from above; a second insulation film which is formed so as to cover the hollow portion; a second electrode which is formed on the second insulation film so as to overlap the hollow portion when seen from above; and a third insulation film which is formed so as to cover the second electrode. The second example further includes a second removal step of removing the protective film on electrode pads of the first electrode and the second electrode when seen from above, in the protective film on the surface formed with the ultrasonic transducer before the thinning step. Accordingly, it is possible to perform the first removal step of removing the protective film on the surface of the chip in (6) in FIG. 3 after the wire bonding step which is performed on the electrode pad in (7) and to protect the surface of the chip formed with the CMUT immediately before the step of coating the surface of the chip, which is formed with the CMUT, with an acoustic lens through pasting in (8).

FIGS. 24A to 24D show cross-sectional views in the step of (11) in FIG. 23. FIG. 24A corresponds to a cut section along line A-A' in FIG. 5, FIG. 24B corresponds to a cut section along line B-B' in FIG. 5, FIG. 24C corresponds to a cut section along line C-C' in FIG. 5, and FIG. 24D corresponds to a cut section along line D-D' in FIG. 5. As can be seen from FIGS. 24C and 24D, openings 2401 and 2402 of a protective film 801 are formed on pad openings 501 and 502 of a CMUT. In the openings of the protective film, for example, when a photosensitive organic polymer material is used as the protective film, it is possible to form the openings 2501 and 2502 of the protective film on the pad openings 501 and 502 through usual photolithography performed on a silicon wafer. That is, in the production method for an ultrasonic probe of the present example, the organic polymer material which is the protective film as a favorable mode is a film having photosensitivity. In this case, even with the polyimide which is mixed with the silane coupling agent as shown in FIG. 18, the residue shown in FIG. 18 does not remain on the pad openings, and therefore, it is possible to improve the reliability of wire bonding.

In addition, even with a case where the protective film is not photosensitive, it is possible to process the protective film by having a mask material, which is formed in order to process the openings 2501 and 2502 of the protective film on the protective film, as a mask. For example when polyimide is used as the protective film, a silicon oxide film is formed on polyimide and patterns of the openings 2501 and 2502 of the protective film are transferred to the silicon oxide film through lithography and etching. Next, it is possible to remove only polyimide on the pad openings 501 and 502 through performing oxygen etching of polyimide by having the silicon oxide film on polyimide as a mask. Next, the silicon oxide film on polyimide can be removed using a buffered hydrofluoric acid without affecting polyimide or the electrode material of the CMUT. In addition, even in a case where residue remains in the pad openings during removal of polyimide, it is possible to remove the residue through processing with the above-described buffered hydrofluoric acid.

Other steps in FIG. 23 are the same as those of the production method shown in Example 1. According to the present example, the protective film on the electrode pad of the chip formed with the CMUT is removed before the wire bonding and the remaining protective film is removed after the wire bonding performed on the electrode pad, and therefore, the protective film is removed immediately before the step of coating the surface of the chip, which is formed with the CMUT, with an acoustic lens. Thus, it is possible to reduce the possibility that the surface of the chip is damaged, compared to the case where the protective film is removed before the wire bonding. This is because there is a possibility that attachment of a foreign substance or the like can occur during chip bonding while no direct force is applied to the surface of the chip in the wire bonding step.

As described above, the characteristic of Example 2 is to insert the step of removing only the protective film on the electrode pad of the CMUT between the step of forming the protective film on the surface of the silicon wafer and the thinning step of the silicon wafer. Accordingly, it is unnecessary to perform the step of removing the protective film before the step of performing the wire bonding on the chip formed with the CMUT and it is possible to protect the chip formed with the CMUT using the protective film immediately before the step of coating the surface of the chip, which is formed with the CMUT, with the acoustic lens. Therefore, it is possible to achieve both controlling damage to one layer of the CMUT and securing operational reliability during driving of the CMUT.

In addition, in the step of (7) in FIG. 23, as described in FIGS. 19A and 19B, it is necessary to bond the flexible wiring substrate to the backing material. For this reason, an electrode pad wiring step of performing wiring on the electrode pad is further provided after the step of providing a sound absorbing material, and the first removal step is set to be performed after the electrode pad wiring step. However, there is also a possibility that the flexible wiring substrate may be etched using oxygen plasma if oxygen plasma processing is performed for removing the protective film in (6). In this case, the order of the processing of the step of (7) in FIG. 23 and the processing of the step of (6) in FIG. 23 maybe changed. Even with polyimide which is mixed with a silane coupling agent, the residue shown in FIG. 18 does not remain on the pad openings, and therefore, it is possible to improve the reliability of wire bonding, which becomes characteristics of this example.

Finally, a configuration example and the role of an ultrasonic diagnosis device which is provided with the ultrasonic probe formed of the ultrasonic transducer of each of the above-described Examples in the ultrasonic diagnosis device will be described with reference to FIG. 25.

In FIG. 25, the ultrasonic diagnosis device is constituted of an ultrasonic diagnosis device main body 2501 and an ultrasonic probe 2502. The ultrasonic diagnosis device main body 2501 is constituted of a transmission/reception separation unit 2503, a transmission unit 2504, a bias unit 2505, a reception unit 2506, a phasing addition unit 2507, an image processing unit 2508, a display unit 2509, a control unit 2510, and an operation unit 2511.

The ultrasonic probe 2502 is a device that transmits and receives an ultrasonic wave with respect to a test object by bringing the ultrasonic wave into contact with the test object, and is produced using an ultrasonic transducer which is produced through the above-described production methods of Examples. An ultrasonic wave is transmitted to a test object from the ultrasonic probe 2502 and a reflected echo signal from the test object is received by the ultrasonic probe 2502. The ultrasonic probe in any of Examples 1 and 2 is electrically connected to the transmission/reception separation unit 2503 to be described later. The transmission unit 2504 and the bias unit 2505 are devices that supply a driving signal to the ultrasonic probe 2502. The reception unit 2506 is a device that receives a reflected echo signal which is output from the ultrasonic probe 2502. The reception unit 2506 further performs processing such as analog/digital conversion with respect to the reflected echo signal which has been received. The transmission/reception separation unit 2503 switches transmission and reception and separates them from each other such that a driving signal is transferred to the ultrasonic probe 2502 from the transmission unit 2504 during transmission, and a reception signal is transferred to the reception unit 2506 from the ultrasonic probe 2502 during reception. The phasing addition unit 2507 is a device that phases and adds the reflected echo signal which has been received. The image processing unit 2508 is a device that constitutes a diagnostic image (for example, tomographic image or blood flow image) based on the reflected echo signal which has been phased and added. The display unit 2509 is a display device that displays the diagnostic image which has been subjected to image processing. The control unit 2510 is a device that controls each of the above-described constituents, and controls transmission/reception of an ultrasonic wave of the ultrasonic probe 2502. The operation unit 2511 is a device that gives an instruction to the control unit 2510. For example, the operation unit 2511 is an input device, such as a track ball, a keyboard, and a mouse.

The present invention is not limited to the above-described Examples and includes various modification examples. For example, the above-described Examples are described in detail for better understanding of the present invention, and are not limited to always having all of the configurations in the description. In addition, a part of the configuration of one Example can be substituted with the configuration of the other Example. In addition, it is possible to add the configuration of the other Example to the one Example. In addition, the other configuration can be added to, deleted from, and substituted with a part of the configuration of each Example.

REFERENCE SIGNS LIST

101: lower electrode
102: hollow portion
103, 602, 603, 604, 605, 606, 608: insulation film
104: upper electrode
105: membrane
401: chip formed with CMUT
402: backing material
403: flexible wiring substrate
404, 406: adhesive layer
405: wire
407: acoustic lens
408: case
501, 502: pad opening
601: semiconductor substrate
607: opening
701: silicon wafer
801: protective film
1001: rear surface of silicon wafer
1002: back grinding tape
1003: grinder
1301: dicing tape
1302: dicing blade
1303: high-pressure water ejection nozzle
1304: high pressure water
1501: pressure applied to surface of chip formed with CMUT
1801: residue
1901: electrode pad of flexible wiring substrate
2401, 2402: opening of protective film
2501: ultrasonic diagnosis device main body
2502: ultrasonic probe
2503: transmission/reception separation unit
2504: transmission unit
2505: bias unit
2506: reception unit 2507: phasing addition unit
2508: image processing unit
2509: display unit
2510: control unit
2511: operation unit

The invention claimed is:

1. A production method for an ultrasonic probe which uses a capacitive ultrasonic transducer formed on a first primary surface of a substrate, comprising:
   a step of forming a protective film on the surface of the ultrasonic transducer which is formed on the first primary surface of the substrate;
   a step of thinning a second primary surface side opposite to the first primary surface of the substrate, after the step of forming a protective film;
   a step of cutting an ultrasonic transducer chip out of the substrate after the step of thinning;
   a step of providing a sound absorbing material on the surface of the ultrasonic transducer chip which is opposite to the surface formed with the ultrasonic transducer, after the cutting step; and
   a first removal step of removing the protective film which is formed on the surface of the ultrasonic transducer, after the step of providing a sound absorbing material.

2. The production method for an ultrasonic probe according to claim 1,
   wherein the ultrasonic transducer includes a first electrode; a first insulation film which is formed on the first electrode; a hollow portion which is formed on the first insulation film so as to overlap the first electrode when seen from above; a second insulation film which is formed so as to cover the hollow portion; a second electrode which is formed on the second insulation film so as to overlap the hollow portion when seen from above; and a third insulation film which is formed so as to cover the second electrode, and
   wherein in the first removal step, the protective film overlapping the hollow portion when seen from above, in the protective film on the surface formed with the ultrasonic transducer, is removed.

3. The production method for an ultrasonic probe according to claim 1,
   wherein the ultrasonic transducer includes a first electrode; a first insulation film which is formed on the first electrode; a hollow portion which is formed on the first insulation film so as to overlap the first electrode when seen from above; a second insulation film which is formed so as to cover the hollow portion; a second electrode which is formed on the second insulation film so as to overlap the hollow portion when seen from above; and a third insulation film which is formed so as to cover the second electrode, and
   wherein before the thinning step, the method further includes a second removal step of removing the protective film on electrode pads of the first electrode and the second electrode when seen from above, in the protective film on the surface formed with the ultrasonic transducer.

4. The production method for an ultrasonic probe according to claim 2,
   wherein the ultrasonic transducer includes a first electrode; a first insulation film which is formed on the first electrode; a hollow portion which is formed on the first insulation film so as to overlap the first electrode when seen from above; a second insulation film which is formed so as to cover the hollow portion; a second electrode which is formed on the second insulation film so as to overlap the hollow portion when seen from above; and a third insulation film which is formed so as to cover the second electrode, and
   wherein before the thinning step, the method further includes a second removal step of removing the protective film on electrode pads of the first electrode and the second electrode when seen from above, in the protective film on the surface formed with the ultrasonic transducer.

5. The production method for an ultrasonic probe according to claim 2, further comprising:
   an electrode pad wiring step of performing wiring on the electrode pad after the step of providing a sound absorbing material,
   wherein the first removal step is performed after the electrode pad wiring step.

6. The production method for an ultrasonic probe according to claim 1,
   wherein the protective film is a film formed of an organic polymer material.

7. The production method for an ultrasonic probe according to claim 6,
   wherein the organic polymer material is a film with photosensitivity.

8. An ultrasonic probe which is produced through the production method for an ultrasonic probe according to claim 1,
   wherein the transducer of the ultrasonic probe includes a first electrode; a first insulation film which is formed on the first electrode; a hollow portion which is formed on the first insulation film so as to overlap the first electrode when seen from above; a second insulation film which is formed so as to cover the hollow portion; a second electrode which is formed on the second insulation film so as to overlap the hollow portion when seen from above; and a third insulation film which is formed so as to cover the second electrode.

9. The ultrasonic probe which is produced through the production method for an ultrasonic probe according to claim 4,
   wherein the protective film is a film formed of an organic polymer material.

10. An ultrasonic diagnosis device comprising:
    the ultrasonic probe according to claim 8; and
    a control unit which controls the ultrasonic probe.

11. An ultrasonic diagnosis device comprising:
    the ultrasonic probe according to claim 9; and
    a control unit which controls the ultrasonic probe.

* * * * *